US012606534B2

(12) United States Patent
Frantz et al.

(10) Patent No.: US 12,606,534 B2
(45) Date of Patent: Apr. 21, 2026

(54) METHOD FOR THE TREATMENT OF KERATIN MATERIALS USING ACID, ESTER OR AMIDE C-GLYCOSIDE DERIVATIVES, AND COSMETIC COMPOSITION CONTAINING SAME

(71) Applicant: L'OREAL, Paris (FR)

(72) Inventors: Marie-céline Frantz, Aulnay-sous-Bois (FR); Maria Dalko, Aulnay-sous-Bois (FR); Alexandre Cavezza, Aulnay-sous-Bois (FR)

(73) Assignee: L'OREAL, Paris (FR)

( * ) Notice: Subject to any disclaimer, the term of this patent is extended or adjusted under 35 U.S.C. 154(b) by 619 days.

(21) Appl. No.: 16/347,315

(22) PCT Filed: Nov. 7, 2017

(86) PCT No.: PCT/EP2017/078485

§ 371 (c)(1),
(2) Date: May 3, 2019

(87) PCT Pub. No.: WO2018/083344

PCT Pub. Date: May 11, 2018

(65) Prior Publication Data

US 2019/0263770 A1 Aug. 29, 2019

(30) Foreign Application Priority Data

Nov. 7, 2016 (FR) ...................................... 1660744
Nov. 6, 2017 (FR) ...................................... 1760399

(51) Int. Cl.

| | |
|---|---|
| ***C07D 309/10*** | (2006.01) |
| ***A61K 8/60*** | (2006.01) |
| ***A61Q 5/08*** | (2006.01) |
| ***A61Q 19/02*** | (2006.01) |
| ***C07D 307/20*** | (2006.01) |

(52) U.S. Cl.

CPC ............. *C07D 309/10* (2013.01); *A61Q 5/08* (2013.01); *A61Q 19/02* (2013.01); *C07D 307/20* (2013.01); *A61K 8/602* (2013.01)

(58) Field of Classification Search

CPC .... A61K 8/602; C07D 307/20; C07D 309/10; C07D 407/12; A61Q 19/02; A61Q 5/08

See application file for complete search history.

(56) References Cited

U.S. PATENT DOCUMENTS

| | | | | |
|---|---|---|---|---|
| 7,862,804 | B2 * | 1/2011 | Rolland | A61K 8/602 424/62 |
| 2005/0002889 | A1 | 1/2005 | Dalko et al. | |
| 2007/0265210 | A1 * | 11/2007 | Breton | A61Q 19/00 514/25 |
| 2018/0133137 | A1 * | 5/2018 | Dalko | C07H 7/02 |

FOREIGN PATENT DOCUMENTS

| | | | |
|---|---|---|---|
| EP | 1 844 757 | A1 | 10/2007 |
| FR | 2 899 468 | A1 | 10/2007 |
| WO | WO 2016/177908 | A2 | 11/2016 |

OTHER PUBLICATIONS

Mata et al., "Reaction of sugars with Meldrum's acid: a route to 3,6-an-hydro-2-deoxyaldono-1,4-lactones", Carbohydrate Research, 201 (1990) 223-231.

* cited by examiner

*Primary Examiner* — Jeffrey T. Palenik
(74) *Attorney, Agent, or Firm* — POLSINELLI PC

(57) ABSTRACT

The present invention relates to a method for the cosmetic treatment of keratin materials, in particular the skin, comprising the application of a composition to the keratin materials, such as the skin, said composition comprising a compound (I), wherein R is as defined in the description and S* is a mono or polysaccharide. In particular, the invention relates to the non-therapeutic cosmetic use of at least one compound of formula (I) as an agent for whitening, lightening and/or depigmenting keratin materials, such as the skin.

6 Claims, No Drawings

METHOD FOR THE TREATMENT OF KERATIN MATERIALS USING ACID, ESTER OR AMIDE C-GLYCOSIDE DERIVATIVES, AND COSMETIC COMPOSITION CONTAINING SAME

CROSS REFERENCE TO RELATED APPLICATIONS

This application is a National Phase filing under 35 U.S.C. § 371 of PCT/EP2017/078485 filed on Nov. 7, 2017; and this application claims priority to Application No. 1660744 filed in France on Nov. 7, 2016, and Application No. 1760399 filed in France on Nov. 6, 2017. The entire contents of each application are hereby incorporated by reference.

The present invention relates to the field of cosmetic products, more particularly intended for caring for keratin materials, especially for caring for facial and/or bodily skin.

The invention relates to C-glycoside compounds comprising an acid, ester or amide group, to a cosmetic composition comprising same, to a preparation process, to the use of said C-glycosides for treating keratin materials and in particular the skin, and to a process for treating keratin materials using said C-glycosides.

More particularly, the present invention is directed towards proposing the use of a novel active agent for efficiently depigmenting and/or lightening, or even bleaching, keratin materials, especially facial and/or bodily skin, and/or for improving the complexion, especially its homogeneity and its radiance.

The colour of human keratin materials, especially of human skin, is mainly determined by the nature and concentration of a pigment, melanin.

The mechanism of melanogenesis, i.e. the mechanism of formation of melanin, is particularly complex and, schematically, involves the following main steps:

Tyrosine→Dopa→Dopaquinone→Dopachrome→Melanin

More particularly, tyrosinase is the essential enzyme which regulates the first steps in the synthesis of pheomelanin and eumelanin, which are the two types of melanin.

The pigmentation of facial and/or bodily skin, and more particularly the pigmentation of the skin, depends on various factors such as environmental factors associated with the seasons of the year, and the origin of the individual.

In addition, at various times in their life, certain people develop on their skin, and more especially on the hands, darker and/or more coloured spots, giving the skin heterogeneity. These spots, which are classified among benign unesthetic pigmentary impairments, are also due to a high concentration of melanin in the skin.

Many processes, mainly with a cosmetic aim, have thus been developed in order to attempt to eliminate or reduce the presence of these unesthetic benign pigmentary impairments. The removal or reduction of the presence of these impairments is customarily founded on applying depigmenting treatments, based on reducing the activity of melanin synthesis in the melanocytes. Depigmenting molecules are to be distinguished from anti-pigmenting molecules which limit the action of the stresses responsible for pigmentation caused, for example, by ultraviolet radiation.

More precisely, a molecule is acknowledged as being depigmenting if, in particular, it interferes with one of the steps of melanin biosynthesis either by inhibiting one of the enzymes involved in melanogenesis, or by intervening as a structural analog of one of the chemical compounds of the melanin synthesis chain, which chain can then be blocked and thus bring about depigmentation.

One of the main routes explored to date is founded on inhibiting tyrosinase. The aim of these treatments is to reduce or even to stop the synthesis of pigment.

The main depigmenting substances known are hydroquinone and derivatives thereof, in particular ethers thereof such as hydroquinone monomethyl ether and monoethyl ether, kojic acid, arbutin, etc.

However, there are major drawbacks associated with the use of the abovementioned depigmenting agents. Specifically, the depigmenting substances may especially show a certain level of instability, low efficiency at low concentration, biological activity affecting other functions, etc.

For example, as regards hydroquinone and derivatives thereof, although these compounds have a certain level of efficacy, they are, unfortunately, not free of side effects, which may make them difficult or even hazardous to use. Thus, the use of harmless topical depigmenting substances with good efficacy is most particularly sought for the purpose of efficiently depigmenting and/or lightening, or even bleaching, keratin materials, especially the skin, and/or for preventing, reducing and/or treating impairment of the complexion of the skin or of the complexion of semi-mucous membranes, i.e. in particular improving the homogeneity of the complexion and/or reviving the radiance of the complexion.

The need thus remains for a novel agent for bleaching keratin materials, especially the skin, which also makes it possible especially to improve the homogeneity of the complexion and to revive the radiance of the complexion, the action of which agent is just as efficient as the known agents, but which does not have the drawbacks thereof, i.e. which is stable, readily formulable, including in aqueous compositions, and/or which is efficient even at low concentration.

In this regard, the Applicant Company has, surprisingly and unexpectedly, discovered that certain particular C-glycoside compounds bearing an acid, ester or amide group have good activity in depigmenting keratin materials and also an action which makes it possible to prevent, reduce and/or treat an impairment of the complexion of the skin or of the complexion of semi-mucous membranes, i.e. in particular an activity which makes it possible to improve the homogeneity of the complexion and to revive the radiance of the complexion, even at low concentration.

Women, and men, currently have, furthermore, a tendency to wish to appear youthful for as long as possible and consequently seek to tone down the signs of ageing of the skin, which are reflected in particular by wrinkles and fine lines, thinning of the epidermis and/or a flaccid and withered skin appearance. In this regard, the advertising and fashion industries mention products for retaining radiant and wrinkle-free skin, signs of youthful skin, for as long as possible, all the more so since physical appearance has an effect on the psyche and/or on morale.

The skin is constituted of two compartments, a surface compartment, the epidermis, and the other deeper compartment, the dermis, which interact. Natural human epidermis is composed mainly of three types of cells, namely keratinocytes, which form the vast majority, melanocytes and Langerhans cells. Each of these types of cells contributes, by virtue of its intrinsic functions, to the essential role played in the body by the skin, in particular the role of protecting the body against external attacking factors, which is known as the "barrier function".

The epidermis is conventionally divided into a basal layer of keratinocytes that constitutes the germinative layer of the epidermis, a spinous layer constituted of several layers of polyhedral cells positioned on the germinative layers, one to three "granular" layers constituted of flattened cells containing distinct cytoplasmic inclusions, keratohyalin granules, and finally the cornified layer (or stratum corneum), constituted of a set of layers of keratinocytes at the terminal stage of their differentiation, known as corneocytes. Corneocytes are anuclear cells mainly constituted of a fibrous material containing cytokeratins, surrounded by a cornified envelope.

The dermis provides the epidermis with a solid support. It is also its nourishing element. It is constituted mainly of fibroblasts and an extracellular matrix composed predominantly of collagen, elastin and a substance known as ground substance. These components are synthesized by the fibroblasts. Leukocytes, mast cells or else tissue macrophages are also found therein. Finally, blood vessels and nerve fibres pass through the dermis. The cohesion between the epidermis and the dermis is provided by the dermo-epidermal junction.

The epidermis is constantly engaged in producing new keratinocytes to compensate for the continuous loss of epidermal cells at the cornified layer. However, in the course of ageing, a decrease in the number of cells in the proliferation phase, and consequently a decrease of the live epidermal layers, may be observed physiologically. By limiting and/or delaying the passing of cells into the differentiation phase, the pool of young cells is maintained.

It is thus important to preserve this pool of proliferative cells, by preventing or delaying their differentiation, in order to contribute towards delaying the onset of the signs of ageing.

During chronological and/or actinic ageing, the dermis and the epidermis undergo numerous modifications and degradations which are reflected, with age, by flaccidness and a loss of suppleness of the skin.

Among the components degraded (in particular collagen and elastin), proteoglycans (also referred to as PGs) and glycosaminoglycans (also referred to as GAGs) are also adversely affected. Specifically, over the course of ageing, the fibroblasts and keratinocytes produce fewer and fewer PGs and GAGs and the synthesis thereof is imperfect. This results in significant disorganization: the deposition of GAGs on the protein backbone forming the PG is abnormal, which results in a decrease in the tonicity of the tissues and thus a loss of suppleness of the skin, and also in particular a lower aridity of these PGs for water and therefore a reduction in moisturization of the tissues.

Restoring a normal production of PGs and GAGs by fibroblasts and keratinocytes contributes partially towards compensating for the loss of moisturization of the skin.

Moreover, with age, a decrease in the expression of proteins playing a key role in the maintenance of the barrier function of the skin, such as filaggrin, membrane transglutaminase or fatty acid desaturase 2 (FADS2), is in particular observed.

The importance of combating the degradation of the various structural proteins of tissues are therefore understood on reading the aforementioned, and possible routes of action for preventing or limiting the consequences of skin ageing are in particular the stimulation of the synthesis of structural molecules of the skin, such as collagen, and in particular collagen III, and also filaggrin, laminin-5, fatty acid desaturase 2 (FADS2) and/or membrane transglutaminase.

The Applicant has surprisingly demonstrated that certain C-glycoside compounds comprising an amide group have anti-ageing and/or moisturizing properties.

A first subject of the invention is a process for treating keratin materials, using at least one cosmetic composition comprising at least one compound of formula (I) below:

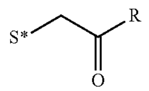

(I)

and also the solvates thereof such as hydrates, the optical and geometric isomers and tautomers thereof and the organic or mineral base or acid salts thereof, in which formula (I):

S* denotes a monosaccharide sugar radical or denotes a polysaccharide sugar radical comprising from 2 to 5 saccharide units, each saccharide unit (the saccharide unit in the case of a monosaccharide or each saccharide unit in the case of polysaccharides) comprising one or more hydroxyl groups optionally substituted with a radical R' chosen from:

i) $(C_1\text{-}C_6)$alkyl; or ii) an acetyl radical;

said monosaccharide or polysaccharide radical not being able to comprise a (hemi)acetal or (hemi) aminal function;

said monosaccharide or polysaccharide radical possibly also comprising one or more amino groups $NR_bR_c$ with $R_b$ and $R_c$, which may be identical or different, representing a hydrogen atom, or an acetyl group, or a protective group for the amino function, such as $(C_1\text{-}C_6)$alkyl(thio)carbonyl;

said monosaccharide or polysaccharide radical being connected to the rest of the molecule by a bond between the $C_1$ carbon atom of one of the sugars of said monosaccharide or polysaccharide radical, this bond possibly being $\alpha$ or $\beta$ anomeric;

R represents a group chosen from:

i) hydroxyl; this hydroxyl can be in the form of an alkoxide $O^+$, $M^+$ with $M^+$ representing a cation such as zinc ($Zn^{2+}$), manganese ($Mn^{2+}$), copper ($Cu^{2+}$), iron ($Fe^{2+}$, $Fe^{3+}$), sodium ($Na^+$), potassium ($K^+$), magnesium ($Mg^{2+}$), calcium ($Ca^{2+}$), or ammonium; (when R is in the form of an alkoxide, it forms, with the carbonyl in the alpha position a carboxylate function $COO^-$, $M^+$ with $M^+$ as previously defined);

ii) saturated or unsaturated $(C_1\text{-}C_{18})$alkoxy;

iii) optionally substituted aryloxy, such as phenyloxy or phenoxy;

iv) optionally substituted aryl$(C_1\text{-}C_6)$alkoxy, such as benzyloxy;

v) a radical (B1):

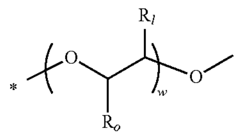

(B1)

in which:

$R_l$ and Ro, independently of one another, denote a hydrogen atom or a methyl radical, it being understood that $R_1$ and $R_o$ cannot simultaneously denote a methyl radical;

w=1 to 10, limits included; or iv) amino —$NR_1R_2$ with $R_1$ and $R_2$, independently of one another, representing:

for $R_1$:

i) a hydrogen atom;

ii) a ($C_1$-$C_{18}$)alkyl group;

iii) a ($C_2$-$C_{18}$)alkenyl group;

iv) an aryl($C_1$-$C_4$)alkyl group optionally substituted in particular with at least one hydroxyl and/or saturated or unsaturated ($C_1$-$C_4$)alkoxy group; or v) an optionally substituted aryl or heteroaryl radical;

for $R_2$:

i) a hydrogen atom;

ii) a ($C_1$-$C_{18}$)alkyl group;

iii) a ($C_2$-$C_{18}$)alkenyl group;

iv) an aryl($C_1$-$C_4$)alkyl group optionally substituted in particular with at least one hydroxyl and/or saturated or unsaturated ($C_1$-$C_4$)alkoxy group;

v) an optionally substituted aryl or heteroaryl radical;

vi) a radical (B'1):

(B'1)

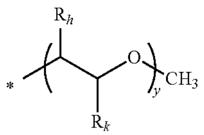

in which:

$R_h$ and $R_k$, independently of one another, denote a hydrogen atom or a methyl radical, it being understood that $R_h$ and $R_k$ cannot simultaneously denote a methyl radical;

y=1 to 10, limits included; or vii) a radical (B'2):

(B'2)

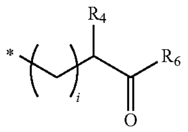

in which:

i=0 or 1;

$R_4$ represents a hydrogen atom or $R_4$ is chosen from the radicals (a1) to (a32) described below:

(a1)

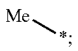

(a2)

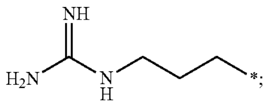

-continued (a3)

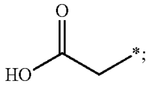

(a4)

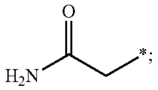

(a5)

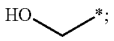

(a6)

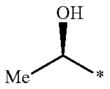

(a7)

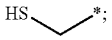

(a8)

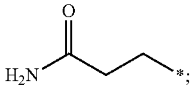

(a9)

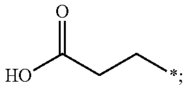

(a10)

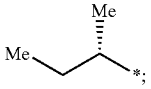

(a11)

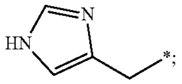

(a12)

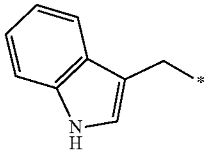

(a13)

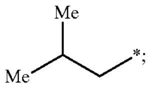

(a14)

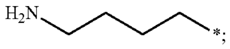

(a15)

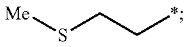

(a16)

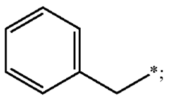

(a17)

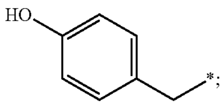

(a18)

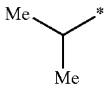

-continued (a19)

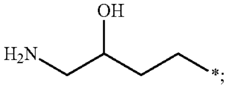

(a20)

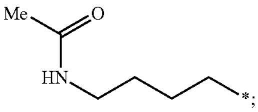

(a21)

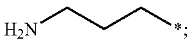

(a22)

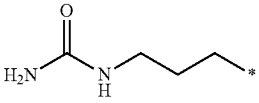

(a23)

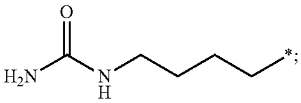

(a24)

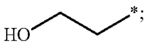

(a25)

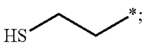

(a26)

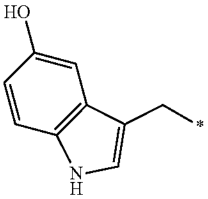

(a27)

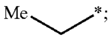

(a28)

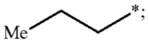

(a29)

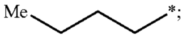

(a30)

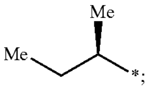

(a31)

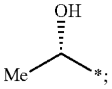

(a32)

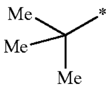

or $R_4$ can form, with $R_1$ and the nitrogen atom which bears $R_1$, a saturated heterocycle of formula A1, A2 or A3:

A1

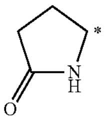

-continued

A2

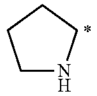

A3

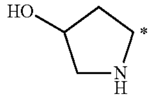

$R_6$ denotes i) a hydroxyl radical —OH;

ii) an alkoxide —$O^-$, $M^+$ with $M^+$ representing a cation such as zinc ($Zn^{2+}$), manganese ($Mn^{2+}$), copper ($Cu^{2+}$), iron ($Fe^{2+}$, $Fe^{3+}$), or an alkali metal cation such as $Na^+$ or $K^+$, or an alkaline-earth metal cation such as $Mg^{2+}$ or $Ca^{2+}$, or an ammonium cation;

iii) a saturated or unsaturated ($C_1$-$C_6$)alkoxy radical;

iv) a radical —$NR_fR_g$ with $R_f$ and $R_g$, which may be identical or different, representing a hydrogen atom or a ($C_1$-$C_6$)alkyl group;

or else $R_1$ and $R_2$ form, with the nitrogen atom to which they are attached, an optionally substituted heterocycloalkyl, such as piperazino, piperidino or morpholino.

One subject of the invention is a process for treating keratin materials, in particular the skin, for depigmenting, lightening and/or bleaching keratin materials, especially facial and/or bodily skin, and/or for preventing, reducing and/or treating an impairment in the complexion of the skin or in the complexion of semi-mucous membranes using at least one compound of formula (I), or at least one cosmetic composition comprising at least one compound of formula (I), said formula (I) being the following formula:

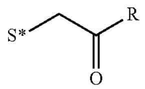

(I)

and also the solvates thereof such as hydrates, the optical and geometric isomers and tautomers thereof and the organic or mineral base or acid salts thereof, in which formula (I):

S* denotes a monosaccharide sugar radical or denotes a polysaccharide sugar radical comprising from 2 to 5 saccharide units, each saccharide unit (the saccharide unit in the case of a monosaccharide or each saccharide unit in the case of polysaccharides) comprising one or more hydroxyl groups optionally substituted with a radical R' chosen from:

i) ($C_1$-$C_6$)alkyl; or ii) an acetyl radical;

said monosaccharide or polysaccharide radical not being able to comprise a (hemi)acetal or (hemi) aminal function;

said monosaccharide or polysaccharide radical possibly also comprising one or more amino groups $NR_bR_c$ with $R_b$ and $R_c$, which may be identical or different, representing a hydrogen atom, or an acetyl group, or a protective group for the amino function, such as ($C_1$-$C_6$)alkyl(thio)carbonyl;

said monosaccharide or polysaccharide radical being connected to the rest of the molecule by a bond between the $C_1$ carbon atom of one of the sugars of said monosaccharide or polysaccharide radical, this bond possibly being α or β anomeric;

R represents a group chosen from:

i) hydroxyl; this hydroxyl can be in the form of an alkoxide $O^-$, $M^+$ with $M^+$ representing a cation such as zinc ($Zn^{2+}$), manganese ($Mn^{2+}$), copper ($Cu^{2+}$), iron ($Fe^{2+}$, $Fe^{3+}$), sodium ($Na^+$), potassium ($K^+$), magnesium ($Mg^{2+}$), calcium ($Ca^{2+}$), or ammonium; (when R is in the form of an alkoxide, it forms, with the carbonyl in the alpha position a carboxylate function $COO^-$, $M^+$ with $M^+$ as previously defined);

ii) saturated or unsaturated ($C_1$-$C_{18}$)alkoxy;

iii) optionally substituted aryloxy, such as phenyloxy or phenoxy;

iv) optionally substituted aryl($C_1$-$C_6$)alkoxy, such as benzyloxy;

v) a radical (B1):

(B1)

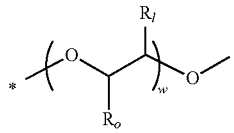

in which:

$R_l$ and Ro, independently of one another, denote a hydrogen atom or a methyl radical, it being understood that $R_l$ and $R_o$ cannot simultaneously denote a methyl radical;

w=1 to 10, limits included; or iv) amino —$NR_1R_2$ with $R_1$ and $R_2$, independently of one another, representing:

for $R_1$:

i) a hydrogen atom;

ii) a ($C_1$-$C_{18}$)alkyl group;

iii) a ($C_2$-$C_{18}$)alkenyl group;

iv) an aryl($C_1$-$C_4$)alkyl group optionally substituted in particular with at least one hydroxyl and/or saturated or unsaturated ($C_1$-$C_4$)alkoxy group; or v) an optionally substituted aryl or heteroaryl radical;

for $R_2$:

i) a hydrogen atom;

ii) a ($C_1$-$C_{18}$)alkyl group;

iii) a ($C_2$-$C_{18}$)alkenyl group;

iv) an aryl($C_1$-$C_4$)alkyl group optionally substituted in particular with at least one hydroxyl and/or saturated or unsaturated ($C_1$-$C_4$)alkoxy group;

v) an optionally substituted aryl or heteroaryl radical;

vi) a radical (B'1):

(B'1)

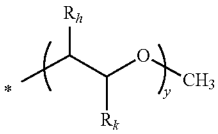

in which:

$R_h$ and $R_k$, independently of one another, denote a hydrogen atom or a methyl radical, it being understood that $R_h$ and $R_k$ cannot simultaneously denote a methyl radical;

y=1 to 10, limits included; or vii) a radical (B'2):

(B'2)

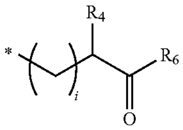

in which:

i=0 or 1;

$R_4$ represents a hydrogen atom or $R_4$ is chosen from the radicals (a1) to (a32) described below:

(a1)

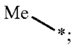

(a2)

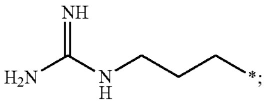

(a3)

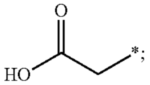

(a4)

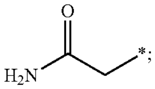

(a5)

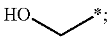

(a6)

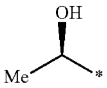

(a7)

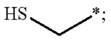

(a8)

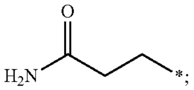

(a9)

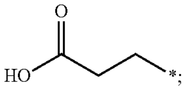

(a10)

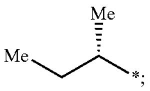

(a11)

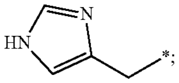

(a12)

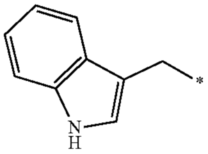

-continued (a13)

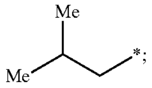

(a14)

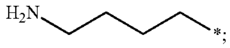

(a15)

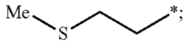

(a16)

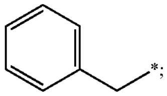

(a17)

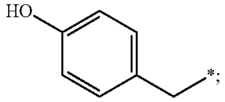

(a18)

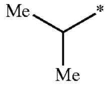

(a19)

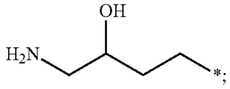

(a20)

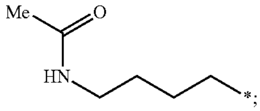

(a21)

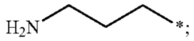

(a22)

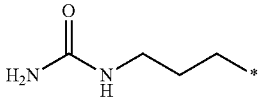

(a23)

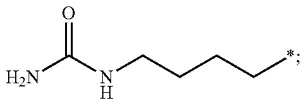

(a24)

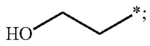

(a25)

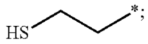

(a26)

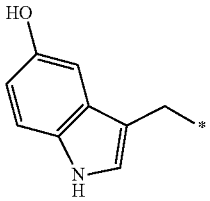

(a27)

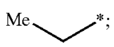

(a28)

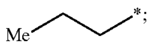

(a29)

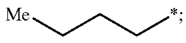

-continued (a30)

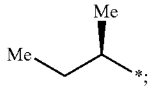

(a31)

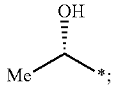

(a32)

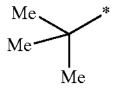

or $R_4$ can form, with $R_1$ and the nitrogen atom which bears $R_1$, a saturated heterocycle of formula A1, A2 or A3:

A1

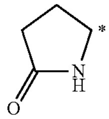

A2

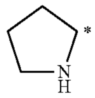

A3

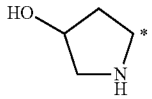

$R_6$ denotes i) a hydroxyl radical —OH;

ii) an alkoxide —$O^-$, $M^+$ with $M^+$ representing a cation such as zinc ($Zn^{2+}$), manganese ($Mn^{2+}$), copper ($Cu^{2+}$), iron ($Fe^{2+}$, $Fe^{3+}$), or an alkali metal cation such as $Na^+$ or $K^+$, or an alkaline-earth metal cation such as $Mg^{2+}$ or $Ca^{2+}$, or an ammonium cation;

iii) a saturated or unsaturated ($C_1$-$C_6$)alkoxy radical;

iv) a radical —$NR_fR_g$ with $R_f$ and $R_g$, which may be identical or different, representing a hydrogen atom or a ($C_1$-$C_6$)alkyl group;

or else $R_1$ and $R_2$ form, with the nitrogen atom to which they are attached, an optionally substituted heterocycloalkyl, such as piperazino, piperidino or morpholino.

The asterisk "*" denotes the point of attachment of the radical to the rest of the compound.

A subject of the present invention is also the cosmetic use of at least one compound of formula (I) and also solvates thereof such as hydrates, optical, geometrical and tautomeric isomers thereof and/or cosmetically acceptable salts thereof, as active agent for depigmenting, lightening and/or bleaching keratin materials, especially facial and/or bodily skin, and/or for preventing, reducing and/or treating an impairment in the complexion of the skin or of the complexion of semi-mucous membranes.

The inventors have, in point of fact, demonstrated that the abovementioned compounds of formula (I) as defined in the present invention have depigmenting, lightening or even bleaching activity on keratin materials, especially the skin.

More particularly, it has been shown, as detailed in the experimental section below, that these compounds of formula (I) reduce melanin synthesis.

In particular, according to this first aspect, the present invention is directed towards protecting the cosmetic use of at least one compound of formula (I) as defined in the present invention or a solvate thereof such as hydrates, optical, geometrical or tautomeric isomers thereof and/or cosmetically acceptable salts thereof, for the treatment of at least one unesthetic benign pigmented impairment.

Also according to this first aspect, the present invention relates to the cosmetic use of at least one compound of formula (I) as defined in the present invention or a solvate thereof such as hydrates, optical, geometrical or tautomeric isomers thereof and/or cosmetically acceptable salts thereof, for improving the homogeneity of the complexion and/or for reviving the radiance of the complexion.

Preferably, the present invention relates to the cosmetic use of at least one compound of formula (IIa), (IIb), (IIc), (IIIa), (IIIb), (IIIc), (IIId) and/or (IIIe) as defined in the present invention below, preferably at least one compound chosen from compounds 1 to 5, and also the solvates thereof such as hydrates, the optical, geometrical or tautomeric isomers thereof and/or the cosmetically acceptable salts thereof, for improving the homogeneity of the complexion and/or for reviving the radiance of the complexion.

The compounds of formula (I) as defined in the present invention or a cosmetically acceptable salt thereof are, at the present time, not known to be used for depigmenting, lightening or even bleaching keratin materials, especially the skin, or for improving the homogeneity of the complexion, or for reviving the radiance of the complexion.

The present invention is also directed towards protecting a non-therapeutic cosmetic treatment process for depigmenting, lightening and/or bleaching keratin materials, especially facial and/or bodily skin and/or for preventing, reducing and/or treating an impairment in the complexion of the skin or of the complexion of semi-mucous membranes, comprising at least one step which consists in applying to said keratin materials and in particular facial and/or bodily skin at least one composition comprising at least one compound of formula (I) or a solvate thereof such as hydrates, optical, geometrical or tautomeric isomers thereof and/or cosmetically acceptable salts thereof as defined in the present invention.

In one particular embodiment, the present invention is also directed towards protecting a non-therapeutic cosmetic treatment process for depigmenting, lightening and/or bleaching keratin materials, especially facial and/or bodily skin, and/or for preventing, reducing and/or treating an impairment in the complexion of the skin or of the complexion of semi-mucous membranes, comprising at least one step which consists in applying to said keratin materials and in particular facial and/or bodily skin at least one composition comprising at least one compound of formula (IIa), (IIb), (IIc), (IIIa), (IIIb), (IIIc), (IIId) and/or (IIIe) as defined in the present invention below, preferably at least one compound chosen from compounds 1 to 5, and also the solvates thereof such as hydrates, the optical, geometrical or tautomeric isomers thereof and/or cosmetically acceptable salts thereof.

For the purposes of the present invention, the term "preventing" or "prevention" means reducing, at least partly, the risk of occurrence of a given phenomenon, i.e., in the present invention, impairment of the complexion of the skin or of the complexion of semi-mucous membranes.

A subject of the present invention is also the cosmetic use of a C-glycoside compound of formula (I) as defined below as an anti-ageing agent and/or moisturizing agent.

Another subject of the invention is novel compounds of formula (I) as defined below.

The compounds of formula (I), and in particular the compounds of formulae (IIa), (IIb), (IIc), (IIIa), (IIIb), (IIIc), (IIId), and/or (IIIe) described below, make it possible to treat keratin materials and in particular the skin, in particular for decreasing and/or delaying the signs of ageing of the skin and/or skin integuments.

The invention also relates to a process for cosmetic treatment of keratin materials, in particular the skin, comprising the application, to said materials, comprising a cosmetic composition comprising at least one compound of formula (I), or in particular at least one compound of formulae (IIa), (IIb), (IIc), (IIIa), (IIIb), (IIIc), (IIId) and/or (IIIe) described below.

For the purposes of the present invention, the term "keratin materials" is intended to mean the skin and skin integuments.

The term "skin" is intended to mean facial and/or bodily skin or the scalp.

The term "integuments" is intended to mean the eyelashes, the eyebrows, the nails and the hair, in particular the eyelashes and the hair.

According to another particular embodiment of the invention, the composition is intended for topical administration to keratin materials such as the skin.

The compounds (I), in particular the compounds of formulae (IIa), (IIb), (IIc), (IIIa), (IIIb), (IIIc), (IIId) and/or (IIIe) described below make it possible in particular to prevent and/or treat the signs of skin ageing.

Among the signs of skin ageing, mention is in particular made of a loss of firmness and/or elasticity and/or tonicity and/or suppleness of the skin, the formation of wrinkles and fine lines, expression lines, in particular on the forehead and in the space between the eyebrows, perioral wrinkles and/or fine lines, and/or slackening in the area around the lips, in particular in the top lip area (area between the top lip and the nose), a dull appearance of the complexion, and the papery appearance of the skin.

The compounds (I), and in particular the compounds of formulae (IIa), (IIb), (IIc), (IIIa), (IIIb), (IIIc), (IIId) and/or (IIIe) described below, advantageously have a glycosaminoglycan-synthesis-stimulating activity and thus make it possible to prevent and/or treat the signs of skin ageing, in particular the loss of firmness and/or of elasticity and/or of tonicity and/or of suppleness of the skin.

The compounds (I), and in particular the compounds of formulae (IIa), (IIb), (IIc), (IIIa), (IIIb), (IIIc), (IIId) and/or (IIIe) described below, also make it possible to prevent and/or treat wrinkles and fine lines, in particular of the face and/or of the body, most particularly of the face and/or of the neck.

The compounds (I), and in particular the compounds of formulae (IIa), (IIb), (IIc), (IIIa), (IIIb), (IIIc), (IIId) and/or (IIIe) described below, also make it possible to maintain and/or stimulate the moisturization and/or combat the drying out of keratin materials such as the skin and/or to maintain the barrier function.

A subject of the invention is also novel compounds of formula (I) as defined below, and also the solvates thereof such as hydrates, the optical, geometrical or tautomeric isomers thereof and/or the cosmetically acceptable salts thereof, in particular and the organic or mineral base or acid salts thereof.

The invention also relates to a process for the cosmetic treatment of keratin materials, in particular of the skin, comprising the application to said materials, comprising a cosmetic composition comprising at least one compound of formula (I) or especially at least one compound of formula (IIa), (IIb), (IIc), (IIIa), (IIIb), (IIIc), (IIId) and/or (IIIe) described below.

For the purposes of the present invention, the term "keratin materials" means the skin and its integuments.

The term "skin" means all of the skin of the body, including the scalp, mucous membranes and semi-mucous membranes.

The term "skin integuments" means bodily hairs, the eyelashes, the hair and the nails.

More particularly, the skin of the neckline, of the neck and of the face, the hands and the armpits are considered in the present invention, and in particular the skin of the face.

According to another particular mode of the invention, the composition is intended for topical administration to keratin materials such as the skin.

Preferably, the hydroxyl radicals of the radical S* are not substituted or are all substituted with the same group R' as previously defined, in particular with an acetyl group.

Preferably, the optional amino group(s) NRbRc of the radical S* denote(s) NHRb with Rb all denoting a hydrogen atom or all denoting an acetyl group.

Preferably, the hydroxyl radicals of the radical S*are not substituted, and the optional amino group(s) NRbRc of the radical S* denote(s) NHRb with Rb all denoting a hydrogen atom or all denoting an acetyl group.

For the purposes of the present invention and unless otherwise indicated:

- the saturated or unsaturated and optionally fused rings may also be optionally substituted;
- the "alkyl" radicals are saturated, linear or branched, generally $C_1$-$C_{18}$, particularly $C_1$-$C_{15}$, hydrocarbon-based radicals, for instance a $C_1$-$C_{14}$ alkyl group, mention may in particular be made of methyl, ethyl, isopropyl, n-propyl, n-butyl, t-butyl, isobutyl, secbutyl, pentyl, isopentyl, neopentyl, n-hexyl, n-heptyl, n-octyl and n-tetradecyl groups;
- the "alkenyl" radicals are linear or branched, unsaturated $C_2$-$C_{18}$ hydrocarbon-based radicals; preferably comprising one or more conjugated or unconjugated double bonds, such as ethylene, propylene, butylene, pentylene, 2-methylpropylene, prenyl and decylene;
- the "aryl" radicals are fused or non-fused monocyclic or polycyclic carbon-based radicals, preferentially comprising from 6 to 30 carbon atoms, and of which at least one ring is aromatic; the aryl radicals are preferentially chosen from phenyl, biphenyl, naphthyl, indenyl, anthracenyl and tetrahydronaphthyl and more particularly aryl denotes phenyl;
- the "alkoxy" radicals are alkyloxy radicals with alkyl as previously defined, the alkyl part of the alkoxy generally being $C_1$-$C_{18}$, preferably $C_1$-$C_{10}$, more preferentially $C_1$-$C_6$, such as methoxy, ethoxy, propoxy and butoxy; when mention is made of unsaturated, this implies that the alkoxy group can represent an alkenyloxy group with alkenyl as previously defined;
- the "cycloalkyl" radicals are $C_4$-$C_8$ cycloalkyl radicals, preferably cyclopentyl and cyclohexyl radicals; the cycloalkyl radicals may be substituted cycloalkyl radicals, in particular substituted with alkyl, alkoxy, carboxylic acid, hydroxyl, amine and ketone groups;
- the "heterocycloalkyl" radicals are saturated or partially unsaturated, nonaromatic heterocyclic radicals comprising from 4 to 8 ring members, which comprise from 1 to 3 heteroatoms, in particular chosen from oxygen, sulfur and nitrogen, preferably the morpholino, piperazino and piperidino radicals; the heterocycloalkyl radicals may be radicals which are substituted, in particular with alkyl, alkoxy, carboxylic acid, hydroxyl, amine and ketone groups;

the "aryl" or "heteroaryl" radicals can be substituted with at least one atom or group borne by at least one carbon atom, chosen from:

i) $C_1$-$C_{10}$ and preferably $C_1$-$C_8$ alkyl, optionally substituted with one or more radicals chosen from the following radicals: hydroxyl, optionally unsaturated ($C_1$-$C_4$)alkoxy, (poly)hydroxy($C_2$-$C_4$)alkoxy, acylamino, amino substituted with two identical or different $C_1$-$C_4$ alkyl radicals optionally carrying at least one hydroxyl group, or it being possible for the two radicals to form, with the nitrogen atom to which they are attached, a saturated or unsaturated and optionally substituted 5- to 7-membered and preferably 5- or 6-membered heterocycle optionally comprising another heteroatom identical to or different from nitrogen;

ii) halogen;

iii) hydroxyl;

iv) $C_1$-$C_4$ alkoxy;

v) $C_1$-$C_{10}$ alkoxycarbonyl;

vi) $C_2$-$C_4$ (poly)hydroxyalkoxy;

vii) $C_2$-$C_4$ alkylcarbonyloxy, preferentially —O-acetyl or acetyloxy;

viii) 5- or 6-membered heterocycloalkyl;

ix) 5- or 6-membered heteroaryl, and optionally substituted with a ($C_1$-$C_4$)alkyl radical, preferentially methyl;

x) amino substituted with one or two $C_1$-$C_6$ alkyl radicals, which may be identical or different, optionally bearing at least: a) one hydroxyl group, b) amino optionally substituted with one or two optionally substituted $C_1$-$C_3$ alkyl radicals, said alkyl radicals possibly forming, with the nitrogen atom to which are attached, a saturated or unsaturated, optionally substituted heterocycle comprising from 5 to 7 ring members, optionally comprising at least one other heteroatom possibly different from nitrogen, c) a quaternary ammonium group $—N^+R'R''R'''$, $Q^-$ for which R', R'' and R''', which may be identical or different, represent a hydrogen atom or a $C_1$-$C_4$ alkyl group; and $Q^-$ represents the anionic counterion such as the halide, d) a 5- or 6-membered heteroaryl radical, and optionally substituted with a ($C_1$-$C_4$) alkyl radical, preferentially methyl;

xi) acylamino (—N(R)—C(O)—R') in which the R radical is a hydrogen atom or a $C_1$-$C_4$ alkyl radical optionally bearing at least one hydroxyl group and the R' radical is a $C_1$-$C_2$ alkyl radical;

xii) carbamoyl ($(R)_2N$—C(O)—) in which the R radicals, which may be identical or different, represent a hydrogen atom or a $C_1$-$C_4$ alkyl radical optionally bearing at least one hydroxyl group;

xiii) alkylsulfonylamino ($R'S(O)_2$—N(R)—) in which the radical R represents a hydrogen atom or a $C_1$-$C_4$ alkyl radical optionally bearing at least one hydroxyl group and the radical R' represents a $C_1$-$C_4$ alkyl radical, or a phenyl radical;

xiv) aminosulfonyl ($(R)_2N$—$S(O)_2$—) in which the R radicals, which may be identical or different, represent a hydrogen atom or a $C_1$-$C_4$ alkyl radical optionally bearing at least one hydroxyl group;

xv) carboxyl in acid or salified form (preferably with an alkali metal or a substituted or unsubstituted ammonium);

xvi) cyano;

xvii) benzyloxycarbonyl;

xviii) polyhaloalkyl, preferentially trifluoromethyl;

xix) a phenylcarbonyloxy group optionally substituted with one or more hydroxyl groups; and xx) a phenyl group optionally substituted with one or more hydroxyl groups;

the "heteroaryl" radicals are radicals comprising, in at least one ring, one or more heteroatoms chosen in particular from O, N and S, preferably O or N, optionally substituted in particular with one or more alkyl, alkoxy, carboxyl, hydroxyl, amine or ketone groups, and at least one ring of which is aromatic. These rings may comprise one or more oxo groups on the carbon atoms of heteroaryl; mention may in particular be made, among the heterocyclic radicals that may be used, of furyl, pyranyl, pyrrolyl, imidazolyl, pyrazolyl, pyridyl thienyl, and pyrimidinyl groups; optionally, the heterocyclic groups are fused groups, such as benzofuranyl, chromenyl, xanthenyl, indolyl, isoindolyl, quinolyl, isoquinolyl, chromanyl, isochromanyl, indolinyl, isoindolinyl, coumarinyl or isocoumarinyl groups, it being possible for these groups to be substituted, in particular with one or more OH groups;

the "protective group" or "PG" of the "hydroxyl" or "amino" function is known by those skilled in the art; mention may be made of the two books "*Protective Groups in Organic Synthesis*", T. W. Greene, published by John Wiley & Sons, NY, 1981, pp. 193-217; "*Protecting Groups*", P. Kocienski, Thieme, 3rd ed., 2005.

In particular, the protective group is chosen from:

($C_1$-$C_6$)alkyl(thio)carbonyl such as formyl, acetyl or t-butylcarbonyl;

(di)(tri)halo($C_1$-$C_6$)alkyl(thio)carbonyl such as trifluoroacetyl (TFA);

($C_1$-$C_6$)alkoxy(thio)carbonyl such as methoxycarbonyl, ethoxycarbonyl, isobutyloxycarbonyl, t-butyloxycarbonyl (BOC), vinyloxycarbonyl, allyloxycarbonyl;

(di)(tri)halo($C_1$-$C_6$)alkoxy(thio)carbonyl such as 2,2,2-trichloroethylcarbonyl;

($C_1$-$C_6$)alkylthio-thiocarbonyl;

(di)(tri)halo($C_1$-$C_6$)alkylthiothiocarbonyl;

(di)($C_1$-$C_6$)(alkyl)aminocarbonyl;

(di)($C_1$-$C_6$)(alkyl)aminothiocarbonyl;

optionally substituted arylcarbonyl such as phenylcarbonyl or 2,4,6-trimethylphenylcarbonyl;

optionally substituted aryloxycarbonyl such as p-nitrophenoxycarbonyl;

optionally substituted aryl($C_1$-$C_6$)alkoxycarbonyl such as benzyloxycarbonyl or Cbz, p-methoxybenzyloxycarbonyl, 3,4-dimethoxybenzyloxycarbonyl, o-nitrobenzyloxycarbonyl, p-nitrobenzyloxycarbonyl, 2-bromobenzyloxycarbonyl (2-bromo-Z) and 2-chlorobenzyloxycarbonyl (2-chloro-Z), 4-nitrobenzyloxycarbonyl (nitro-Z), heteroaryl($C_1$-$C_6$)alkoxycarbonyl such as 9-fluorenylmethoxycarbonyl (FMOC) or nicotinoyl;

(di)($C_1$-$C_6$)(alkyl)aminocarbonyl, for instance dimethylaminocarbonyl;

($C_1$-$C_6$)(alkyl)arylaminocarbonyl;

carboxyl;

optionally substituted aryl such as phenyl, dibenzosuberyl or 1,3,5-cycloheptatrienyl;

optionally substituted heteroaryl; in particular including the following cationic or non-cationic heteroaryls comprising from 1 to 4 heteroatoms:

i) 5-, 6- or 7-membered monocyclic groups such as furanyl or furyl, pyrrolyl or pyrryl, thiophenyl or thienyl, pyrazolyl, oxazolyl, oxazolium, isoxazolyl, isoxazolium, thiazolyl, thiazolium, isothiazolyl, isothiazolium, 1,2,4-triazolyl, 1,2,4-triazolium, 1,2,3-triazolyl, 1,2,3-triazolium, 1,2,4-oxazolyl, 1,2,4-oxazolium, 1,2,4-thiadiazolyl, 1,2,4-thiadiazolium, pyrylium, thiopyridyl, pyridinium, pyrimidinyl, pyrimidinium, pyrazinyl, pyrazinium, pyridazinyl, pyridazinium, triazinyl, triazinium, tetrazinyl, tetrazinium, azepine, azepinium, oxazepinyl, oxazepinium, thiepinyl, thiepinium, imidazolyl, imidazolium;

ii) 8- to 11-membered bicyclic groups such as indolyl, indolinium, benzimidazolyl, benzimidazolium, benzoxazolyl, benzoxazolium, dihydrobenzoxazolinyl, benzothiazolyl, benzothiazolium, pyridoimidazolyl, pyridoimidazolium, thienocycloheptadienyl, these monocyclic or bicyclic groups being optionally substituted with one or more groups such as ($C_1$-$C_4$)alkyl, for instance methyl, or polyhalo($C_1$-$C_4$)alkyl, for instance trifluoromethyl;

iii) or the following tricyclic ABC group:

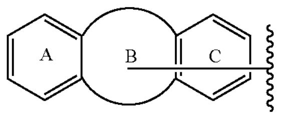

in which the two rings A and C optionally comprise a heteroatom, and ring B is a 5-, 6- or 7-membered ring, particularly a 6-membered ring, and contains at least one heteroatom, for instance piperidyl or pyranyl;

optionally cationic, optionally substituted heterocycloalkyl, the heterocycloalkyl group in particular representing a saturated or partially saturated 5-, 6- or 7-membered monocyclic group comprising from 1 to 4 heteroatoms chosen from oxygen, sulfur and nitrogen, such as di/tetrahydrofuranyl, di/tetrahydrothiophenyl, di/tetrahydropyrrolyl, di/tetrahydropyranyl, di/tetra/hexahydrothiopyranyl, dihydropyridyl, piperazinyl, piperidinyl, tetramethylpiperidinyl, morpholinyl, di/tetra/hexahydroazepinyl, di/tetrahydropyrimidinyl, these groups being optionally substituted with one or more groups such as ($C_1$-$C_4$)alkyl, oxo or thioxo, preferably tetrahydropyranyl THP; or the heterocycle represents the following group:

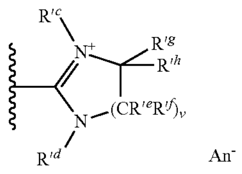

in which $R'^c$, $R'^d$, $R'^e$, $R'^f$, $R'^g$ and $R'^h$, which may be identical or different, represent a hydrogen atom or a ($C_1$-$C_4$)alkyl group, or alternatively two groups $R'^g$ with $R'^h$, and/or $R'^e$ with $R'^f$ form an oxo or thioxo group, or alternatively $R'^g$ with $R'^e$ together form a cycloalkyl; and v represents an integer between 1 and 3 inclusive; preferentially, $R'^c$ to $R'^h$ represent a hydrogen atom; and $An^-$ represents a counterion;

- isothiouronium $—C(NR'^cR'^d)=N^+R'^eR'^f$; $An^-$ with $R'^c$, $R'^d$, $R'^e$ and $R'^f$, which may be identical or different, representing a hydrogen atom or a $(C_1\text{-}C_4)$alkyl group; preferentially, $R'^c$ to $R'^f$ represent a hydrogen atom; and $An^-$ represents a counterion;
- isothiourea $—C(NR'^cR'^d)=NR'^e$; with $R'^c$, $R'^d$ and $R'^e$ as previously defined;
- optionally substituted (di)aryl$(C_1\text{-}C_4)$alkyl or triaryl$(C_1\text{-}C_4)$alkyl such as 9-anthracenylmethyl, phenylmethyl (benzyl), diphenylmethyl or triphenylmethyl optionally substituted with one or more groups, in particular chosen from halogen, $(C_1\text{-}C_4)$alkyl, $(C_1\text{-}C_4)$alkoxy such as methoxy, hydroxyl, $(C_1\text{-}C_4)$alkylcarbonyl, (di) $(C_1\text{-}C_4)$(alkyl)amino such as dimethylamino, nitro;
- optionally substituted (di)heteroaryl$(C_1\text{-}C_4)$alkyl or triheteroaryl$(C_1\text{-}C_4)$alkyl, the heteroaryl group in particular being cationic or noncationic, 5- or 6-membered monocyclic comprising from 1 to 4 heteroatoms chosen from nitrogen, oxygen and sulfur, such as pyrrolyl, furanyl, thiophenyl, pyridyl, pyridyl N-oxide such as 4-pyridyl or 2-pyridyl-N-oxide, pyrylium, pyridinium or triazinyl groups, optionally substituted with one or more groups such as alkyl, particularly methyl; advantageously, the (di)heteroaryl$(C_1\text{-}C_4)$alkyl is (di)heteroarylmethyl or (di)heteroarylethyl;
- $CR^1R^2R^3$ with $R^1$, $R^2$ and $R^3$, which may be identical or different, representing a halogen atom, such as (tri)(di) halo$(C_1\text{-}C_4)$alkyl such as 2,2,2-trichloroethyl or a group chosen from:
  - $(C_1\text{-}C_4)$alkyl such as methyl;
  - $(C_1\text{-}C_4)$alkoxy;
  - optionally substituted aryl such as phenyl optionally substituted with one or more groups, for instance $(C_1\text{-}C_4)$alkyl, $(C_1\text{-}C_4)$alkoxy or hydroxyl;
  - optionally substituted heteroaryl such as thiophenyl, furanyl, pyrrolyl, pyranyl or pyridyl, optionally substituted with a $(C_1\text{-}C_4)$alkyl group;
  - $P(Z^1)R'^1R'^2R'^3$ with $R'^1$ and $R'^2$, which may be identical or different, representing a hydroxyl, $(C_1\text{-}C_4)$alkoxy or alkyl group, $R'^3$ representing a hydroxyl or $(C_1\text{-}C_4)$alkoxy group, and $Z^1$ representing an oxygen or sulfur atom;
- $(C_2\text{-}C_6)$alkylene, in particular allyl $H_2C=CH—CH_2—$;
- optionally substituted arylsulfonyl such as p-toluenesulfonyl (Tos);
- sterically hindered cycloalkyl such as the adamantyl group;
- sterically hindered cycloalkyloxy(thio)carbonyl such as 1-adamantyloxycarbonyl (Adoc) or 1-(adamantyl)-1-methylethoxycarbonyl (Adpoc);
- optionally substituted $(C_1\text{-}C_4)$alkoxy$(C_1\text{-}C_4)$alkyl such as methoxymethyl (MOM), ethoxyethyl (EOM) and isobutoxymethyl;
- (tri)(di)halo$(C_1\text{-}C_4)$alkyl such as 2,2,2-trichloroethyl;
- $R_eR_fR_gSi—$ with $R_e$, $R_f$, and $R_g$, which may be identical or different, representing a $(C_1\text{-}C_6)$alkyl group, optionally substituted aryl group, optionally substituted (di) aryl$(C_1\text{-}C_4)$alkyl group, optionally substituted triaryl $(C_1\text{-}C_4)$alkyl group, such as benzyl, in particular chosen from trimethylsilyl or TMS, triethylsilyl, isopropyldimethylsilyl, tert-butyldimethylsilyl or TBDMS, (triphenylmethyl)dimethylsilyl, tbutyldiphenylsilyl, methyldiisopropylsilyl, methyl(di-t-butyl)silyl, tribenzylsilyl, tri-p-xylylsilyl, triisopropylsilyl, triphenylsilyl;
- or else two contiguous hydroxyl groups can be protected with an alkylene group $*—C(R^l)(R^m)—(C(R^k)(R^j)_q—*$ as drawn below:

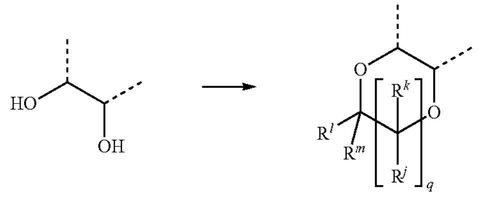

with $R^j$, $R^k$, $R^l$, and $R^m$, which may be identical or different, representing a hydrogen atom or a $(C_1\text{-}C_4)$ alkyl, (poly)halo$(C_1\text{-}C_4)$alkyl, optionally substituted aryl such as phenyl, aryl$(C_1\text{-}C_4)$alkyl such as benzyl, (poly)halo$(C_1\text{-}C_4)$alkoxy, $(C_1\text{-}C_4)$alkoxy, halogen, (di) $(C_1\text{-}C_4)$(alkyl)amino or hydroxyl group, or else two $R^j$ and $R^k$ and/or $R^l$, and $R^m$ groups form, together with the carbon atom which bears them, an oxo group or a (hetero)cycloalkyl group such as cyclohexyl or cyclopropyl; q is 0, 1, 2 or 3, preferably $*—C(R^l)(R^m)—(C(R^k)(R^j))_q—*$ represents a methylene, ethylene, propylene, dimethylmethylene, $*—C(CH_3)_2—*$ or diphenylmethylene $*—C(Ph)_2\text{-}*$, cyclopentylidene, cyclohexylidene, cycloheptylidene, benzylidene, p-methoxybenzylidene, 2,4-dimethoxybenzylidene, methoxymethylene and ethoxymethylene.

The asterisk "*" denotes the point of attachment of the radical to the rest of the compound.

In the context of the present invention, the sugar radicals, whether they are monosaccharide or polysaccharide radicals, do not contain an acetal group or a hemiacetal group or an aminal group or a hemiaminal group.

The acceptable solvates of the compounds used in the present invention comprise conventional solvates such as those formed during the last step of the preparation of said compounds due to the presence of solvents. Mention may be made, by way of example, of the solvates due to the presence of water (hydrates) or of linear or branched alcohols, such as ethanol or isopropanol.

The salts of the compounds (I) which comprise at least one acid function can be chosen from metal salts, for example aluminium ($Al^{3+}$), zinc ($Zn^{2+}$), manganese ($Mn^{2+}$) or copper ($Cu^{2+}$); alkali metal salts, for example lithium ($Li^+$), sodium ($Na^+$) or potassium ($K^+$); or alkaline-earth metal salts, for example calcium ($Ca^{2+}$) or magnesium ($Mg^{2+}$). They can also be ammonium derivatives of formula $NH_4^+$ or organic salts such as ammonium's of formula $Y_3NH^+$, $NY_3$ denoting an organic amine, the Y radicals being identical or different, it being possible for two or three Y radicals to form, in pairs, a ring with the nitrogen atom which carries them or it being possible for $NY_3$ to denote an aromatic amine. The organic amines are for example alkylamines, for instance methylamine, dimethylamine, trimethylamine, triethylamine or ethylamine, or hydroxyalkylamines, for instance 2-hydroxyethylamine, bis(2-hydroxyethyl) amine or tri-(2-hydroxyethyl)amine, or cycloalkylamines, for instance bicyclohexylamine or glucamine, piperidine, or pyridines and the like, for example collidine, quinine or quinoline, or amino acids which are basic in nature, for instance lysine or arginine.

The salts of the compounds of formula (I) which comprise at least one amine function can be salts of an organic acid such as citric acid, lactic acid, tartaric acid, aspartic acid, glutamic acid, acetic acid, formic acid, trifluoroacetic acid, hydrochloric acid, glycolic acid or malic acid.

In the case where the compounds according to the invention are in salt form, the cations are of course in an amount which ensures the electro-neutrality of the compounds of formula (I).

The salts of the compounds of formula (I) which contain at least one acid function can advantageously be chosen from the metal salts $Cu^{2+}$, $Mn^{2+}$ and $Zn^{2+}$, the alkali metal salts $Li^+$, $Na^+$ and $K^+$ and the alkaline-earth metal salts $Ca^{2+}$ and $Mg^{2+}$.

According to another variant, the salts of the compounds of formula (I) according to the invention which comprise at least one acid function can advantageously be chosen from ammoniums, preferably from the salts of amino acids which are basic in nature, for instance lysine or arginine or from diethanolamine salts or triethanolamine salts.

Preferably, the compounds (I) which comprise at least one acid function are in the form of sodium salts $Na^+$.

Preferably, the compounds (I) which comprise at least one acid function are in the form of potassium salts $K^+$.

Preferably, the compounds (I) which comprise at least one acid function are in the form of calcium salts $Ca^+$.

According to one particular embodiment of the invention, the compounds of formula (I) are such that R represents a hydroxyl radical or an alkoxide radical $O^-$, $M^+$ with $M^+$ representing a cation such as zinc ($Zn^{2+}$), manganese ($Mn^{2+}$), copper ($Cu^{2+}$), iron ($Fe^{2+}$, $Fe^{3+}$), sodium ($Na^+$), potassium ($K^+$), magnesium ($Mg^{2+}$), calcium ($Ca^{2+}$), or ammonium.

As an example of compounds of formula (I) according to this embodiment, mention may particularly be made of the following compound and also the salts, isomers and solvates thereof:

compound 1

Chiral

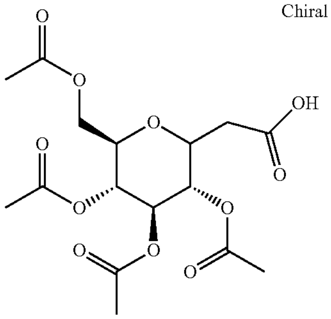

S* = D-Glucose

According to another particular embodiment of the invention, the compounds of formula (I) are such that R represents a preferably saturated $(C_1-C_{18})$alkoxy group, more preferentially a $(C_1-C_6)$alkoxy group, in particular ethoxy.

According to another particular embodiment of the invention, the compounds of formula (I) are such that, taken together or separately, R represents a radical (B1):

(B1)

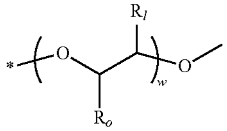

in which:

$R_l$ and Ro, independently of one another, denote a hydrogen atom or a methyl radical, it being understood that $R_l$ and $R_o$ cannot simultaneously denote a methyl radical;

w=1 to 10, preferably from 1 to 5, more preferentially from 1 to 3, limits included.

According to another particular embodiment of the invention, the compounds of formula (I) are such that, taken together or separately, R represents an amino group $—NR_1R_2$ with $R_1$ and $R_2$, independently of one another, representing:

i) a hydrogen atom;

ii) a $(C_1-C_{18})$alkyl group, preferably $(C_1-C_{16})$alkyl such as $(C_1-C_4)$alkyl and/or $(C_8-C_{16})$alkyl;

iii) or else $R_1$ and $R_2$ form, with the nitrogen atom to which they are attached, an optionally substituted heterocycloalkyl, such as piperazino, piperidino or morpholino.

According to this embodiment, $R_1$ and $R_2$ preferably represent, independently of one another:

i) a hydrogen atom;

ii) a $(C_1-C_{18})$alkyl group, preferably $(C_1-C_{16})$alkyl and in particular a methyl or n-tetradecyl radical.

According to a first form of this embodiment, $R_1$ and $R_2$ are identical and chosen from i) a hydrogen atom;

ii) a $(C_1-C_{18})$alkyl group, preferably $(C_1-C_4)$alkyl and in particular a methyl radical.

As an example of a compound of formula (I) according to this embodiment, mention may for example be made of the compounds below, and also the salts, isomers and solvates thereof:

compound 3

Chiral

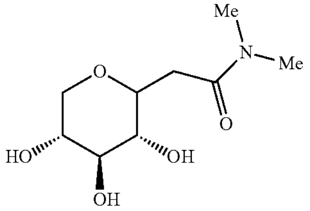

S* = D-xylose compound 4

Chiral

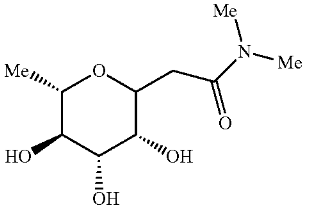

S* = L-rhamnose

According to a second form of this variant, $R_1$ denotes a hydrogen atom and $R_2$ denotes a $(C_1-C_{18})$alkyl group, preferably $(C_1-C_{16})$alkyl and in particular a $(C_8-C_{16})$alkyl radical such as n-tetradecyl.

By way of example of compound of formula (I) according to this embodiment, mention may be made, for example, of compound 5 below, and also the salts, isomers or solvates thereof:

compound 5

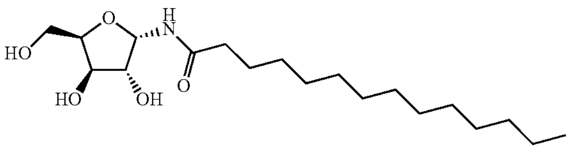

S* = D-xylofuranose

According to another particular embodiment of the invention, the compounds of formula (I) are such that, taken together or separately, R represents an amino group —$NR_1R_2$ with $R_1$ and $R_2$, independently of one another, representing:

for $R_1$:

i) a hydrogen atom; or ii) a ($C_1$-$C_{18}$)alkyl group, preferably ($C_1$-$C_4$)alkyl; more preferentially methyl; preferably, $R_1$ represents a hydrogen atom;

for $R_2$:

a radical (B'1) such as:

(B'1)

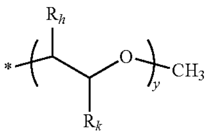

in which:

$R_h$ and $R_k$, independently of one another, denote a hydrogen atom or a methyl radical, it being understood that $R_h$ and $R_k$ cannot simultaneously denote a methyl radical;

y=1 to 10, preferably from 1 to 5, more preferentially from 1 to 3, limits included.

According to another particular embodiment of the invention, the compounds of formula (I) are such that, taken together or separately, R represents an amino group —$NR_1R_2$ with $R_1$ and $R_2$, independently of one another, representing:

for $R_1$:

i) a hydrogen atom; or ii) a ($C_1$-$C_{18}$)alkyl group, preferably ($C_1$-$C_4$)alkyl; more preferentially methyl; preferably, $R_1$ represents a hydrogen atom;

for $R_2$:

a radical (B'2):

(B'2)

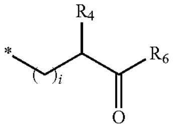

in which:

i=0 or 1;

$R_4$ represents a hydrogen atom or $R_4$ is chosen from the radicals (a1) to (a32) described below:

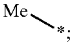
(a1)

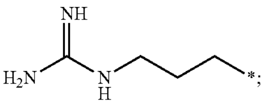
(a2)

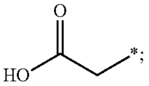
(a3)

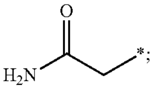
(a4)

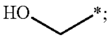
(a5)

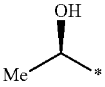
(a6)

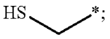
(a7)

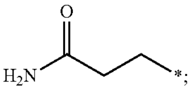
(a8)

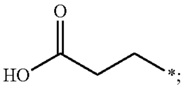
(a9)

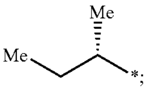
(a10)

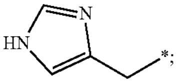
(a11)

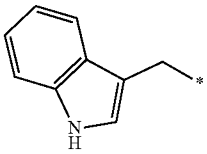
(a12)

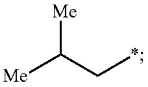
(a13)

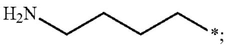
(a14)

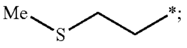
(a15)

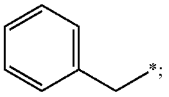
(a16)

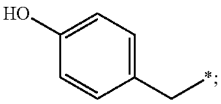
(a17)

-continued (a18)

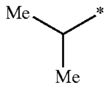

(a19)

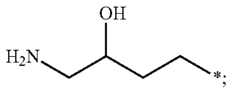

(a20)

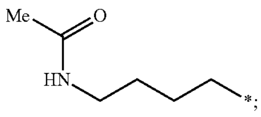

(a21)

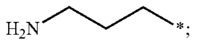

(a22)

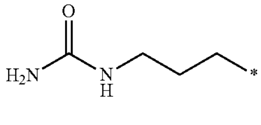

(a23)

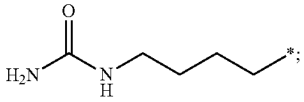

(a24)

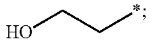

(a25)

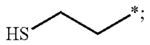

(a26)

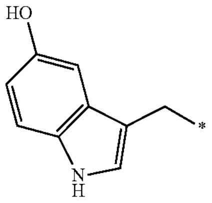

(a27)

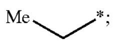

(a28)

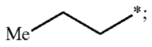

(a29)

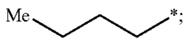

(a30)

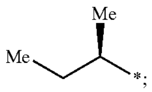

(a31)

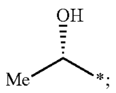

(a32)

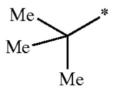

or $R_4$ can also form, with $R_1$ and the nitrogen atom which bears $R_1$, a saturated heterocycle of formula A1, A2 or A3:

A1

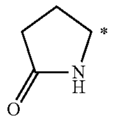

A2

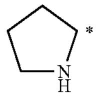

A3

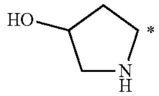

$R_6$ denotes i) a hydroxyl radical —OH;

ii) an alkoxide —$O^-$, $M^+$ with $M^+$ representing a cation such as zinc ($Zn^{2+}$), manganese ($Mn^{2+}$), copper ($Cu^{2+}$), iron ($Fe^{2+}$, $Fe^{3+}$), or an alkali metal cation such as $Na^+$ or $K^+$, or an alkaline-earth metal cation such as $Mg^{2+}$ or $Ca^{2+}$, or an ammonium cation;

iii) a saturated or unsaturated ($C_1$-$C_6$)alkoxy radical; or iv) a radical —$NR_fR_g$ with $R_f$ and $R_g$, which may be identical or different, representing a hydrogen atom or a ($C_1$-$C_6$)alkyl group.

According to another particular embodiment of the invention, the compounds of formula (I) are such that, taken together or separately, R represents an amino group —$NR_1R_2$ with $R_1$ and $R_2$, independently of one another, representing:

for $R_1$:

i) a hydrogen atom;

ii) a ($C_1$-$C_{18}$)alkyl group, preferably ($C_1$-$C_4$)alkyl; more preferentially methyl; and preferably $R_1$ represents a hydrogen atom;

for $R_2$:

i) an optionally substituted aryl or heteroaryl radical, in particular an optionally substituted phenyl radical;

iii) an optionally substituted heteroaryl radical;

iv) an aryl($C_1$-$C_4$)-alkyl radical, in particular a phenyl-($C_1$-$C_4$)alkyl radical; and preferably $R_2$ denotes an optionally substituted phenyl radical.

According to another particular embodiment of the invention, the compounds of formula (I) are such that, taken together or separately, R represents an optionally substituted aryloxy group, in particular an optionally substituted phenoxy group.

According to another particular embodiment of the invention, the compounds of formula (I) are such that, taken together or separately, R represents an optionally substituted aryl($C_1$-$C_6$)alkoxy group, such as an optionally substituted benzyloxy group.

It is understood that, for the compounds of formula (I) as previously defined, when S* represents a monosaccharide radical, then it can be in pyranose form (the sugar heterocycle which constitutes it comprises 6 ring members) or furanose form (the sugar heterocycle which constitutes it comprises 5 ring members); and when S* represents a polysaccharide radical, it comprises the sequence of 2 to 5 saccharide units, which may be identical to or different from one another, which may be in furanose or pyranose form. Preferably, when S* represents a polysaccharide radical, the polysaccharide is a disaccharide which results from the linking of 2 pyranose units or the linking of a saccharide unit in furanose form and a unit in pyranose form or the linking of a saccharide unit in pyranose form and a unit in furanose form; whether it is for the monosaccharide or polysaccharide radical, each saccharide unit may be in levorotatory L or dextrorotatory D form, and in α or β anomeric form.

According to one preferred embodiment, the sugar radical S* represents a monosaccharide radical in which the heterocycle constituting it contains 4 or 5 carbon atoms, of formula S*' below:

S*'

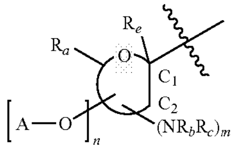

$R_a$ representing a hydrogen atom, a $(C_1-C_4)$alkyl group such as methyl or a (poly)hydroxy$(C_1-C_4)$alkyl group such as hydroxymethyl or 1,2-dihydroxyethyl, the hydroxyl function(s) of the (poly)hydroxy$(C_1-C_4)$alkyl group being substituted with A as defined below;

it being understood that the $R_a$ radical is in the $C_5$ position if the sugar unit is in pyranose form or in the $C_4$ position if it is in furanose form;

$R_b$ representing a hydrogen atom or a $(C_1-C_4)$alkyl group, preferably hydrogen;

$R_c$ representing a hydrogen atom, or a protective group for the amine function, such as $R_d$—C(O)—, identical in the case of several hydroxyl functions, with $R_d$ representing a $(C_1-C_4)$alkyl group, $R_c$ preferably representing an acetyl group $CH_3$—C(O)—;

$R_e$ representing a hydrogen atom or a —$CH_2$—O-A group;

A representing a hydrogen atom, a $(C_1-C_6)$alkyl group or a hydroxyl-function-protective group, such as $R_d$—C(O)— as defined above and in particular acetyl $CH_3$—C(O)—, or else, when n is greater than or equal to 2 and two groups A-O are contiguous, then two A groups can together form a linear or branched $(C_1-C_6)$alkylene chain;

preferably, all the protective groups for A are identical;

n is equal to 1, 2 or 3 and m is equal to 0 or 1.

According to a particular form of the invention, m is zero.

According to another preferred embodiment, the sugar radical S* represents a polysaccharide radical constituted of 2 to 5 saccharide units, in particular of 2 to 3 and preferably of 2 saccharide units, linked together via an oxygen atom (oxy), of 1→4 ($C_1$ of one saccharide unit→$C_4$ of the other saccharide unit) or 1→3 ($C_1$ of one saccharide unit→$C_3$ of the other saccharide unit) or 1→6 ($C_1$ of one saccharide unit→$C_6$ of the other saccharide unit), each saccharide unit of which is constituted of a heterocycle comprising 4 or 5 carbon atoms, of formula S*" below:

S*"

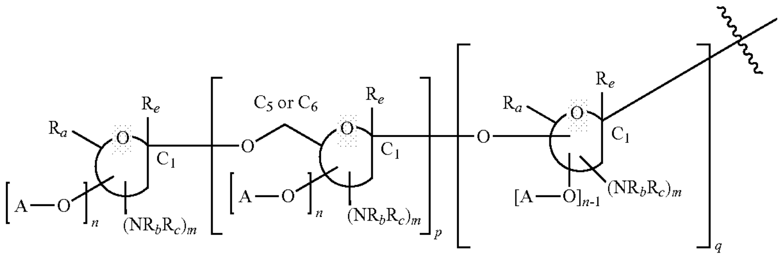

in which formula S*", p and q represent integers of inclusively between 0 and 4 with p+q inclusively between 1 and 4, particularly between 1 and 2, preferentially p+q=1; $R_a$, which may be identical or different, are as defined previously, $R_b$, which may be identical or different, are as defined previously, $R_c$, which may be identical or different, are as defined previously, $R_e$, which may be identical or different, are as defined previously, A, which may be identical or different, are as defined previously, m, which may be identical or different, are as defined previously, n, which may be identical or different, are as defined previously, it being understood that the two sugar units between the square brackets q and p can interchange, i.e. can represent the chain below:

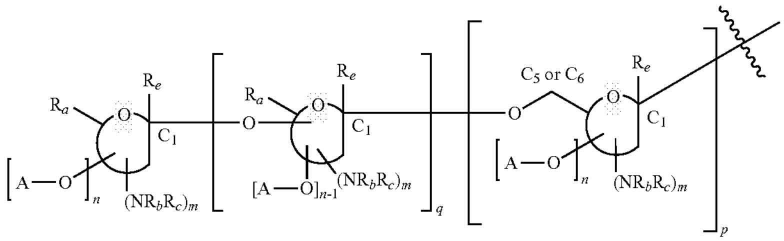

According to one preferred variant of the invention, the compounds of formula (I) are such that:

S* represents a monosaccharide sugar radical, in pyranose or furanose form, said monosaccharide being chosen from: glucose, galactose, mannose, xylose, lyxose, fucose, arabinose, rhamnose, quinovose, fructose, sorbose, talose, N-acetylglucosamine, N-acetylgalactosamine, glucosamine and galactosamine; or S* represents a disaccharide chosen from: lactose, maltulose, palatinose, lactulose, amygdalose, turanose, cellobiose, isomaltose, rutinose and maltose, preferably S* represents a sugar radical chosen from glucose, galactose, mannose, xylose, rhamnose, fructose, sorbose, N-acetylglucosamine, N-acetylgalactosamine, glucosamine, galactosamine, lactose, cellobiose and maltose, and preferably chosen from glucose, xylose and rhamnose;

said radical S* comprising one or more radicals —$OR_s$ and optionally one or two radicals —$NHR'_s$, said monosaccharide or disaccharide radical being connected to the rest of the molecule by a bond between the $C^1$ carbon atom of the sugar or one of the sugars and this bond possibly being α or β anomeric;

R represents:

i) a hydroxyl radical; can be in carboxylate form $O^-$, $M^+$ with $M^+$ representing a cation such as zinc ($Zn^{2+}$), manganese ($Mn^{2+}$), copper ($Cu^{2+}$), iron ($Fe^{2+}$, $Fe^{3+}$), sodium ($Na^+$), potassium ($K^+$), magnesium ($Mg^{2+}$), calcium ($Ca^{2+}$), or ammonium;

ii) a $(C_1\text{-}C_{18})$alkoxy group, preferably $(C_2\text{-}C_6)$alkoxy such as ethoxy;

iii) a $(C_2\text{-}C_{18})$alkenyloxy, preferably $(C_2\text{-}C_6)$alkenyloxy, such as prenyloxy;

iv) an optionally substituted aryloxy radical, such as phenyloxy or phenoxy;

v) an aryl$(C_1\text{-}C_6)$alkoxy radical optionally substituted in particular with at least one hydroxyl and/or saturated or unsaturated $(C_1\text{-}C_4)$alkoxy group, in particular an aryl$(C_1\text{-}C_4)$alkoxy radical such as benzyloxy;

v) a radical such as:

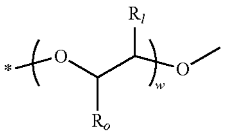

in which:

$R_l$ and Ro, independently of one another, denote a hydrogen atom or a methyl radical, it being understood that $R_l$ and $R_o$ cannot simultaneously denote a methyl radical;

w=1 to 10, preferably 1 to 5, preferentially from 1 to 3, limits included.

vi) an amino radical —$NR_1R_2$ with $R_1$ and $R_2$, independently of one another, representing:

for $R_1$:

a hydrogen atom;

a saturated or unsaturated $(C_1\text{-}C_{18})$alkyl group, which is preferably saturated and more preferentially a saturated $C_1\text{-}C_6$ group such as methyl;

for $R_2$:

a hydrogen atom;

a saturated or unsaturated $(C_1\text{-}C_{18})$alkyl group, which is preferably saturated and more preferentially a saturated $C_1\text{-}C_6$ group such as methyl;

an aryl$(C_1\text{-}C_4)$alkyl group optionally substituted in particular with at least one hydroxyl and/or saturated or unsaturated $(C_1\text{-}C_4)$alkoxy group;

an aryl or heteroaryl radical, which is optionally substituted, preferably with one or more $(C_1\text{-}C_6)$ alkyl, hydroxyl, $C_1\text{-}C_4$ alkoxy, $C_1\text{-}C_6$ alkoxycarbonyl, or carboxy groups, which may be identical or different;

a radical such as:

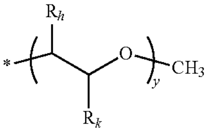

in which:

$R_h$ and $R_k$, independently of one another, denote a hydrogen atom or a methyl radical, it being understood that $R_h$ and $R_k$ cannot simultaneously denote a methyl radical;

y=1 to 10, preferably 1 to 5, preferentially from 1 to 3;

a radical such as:

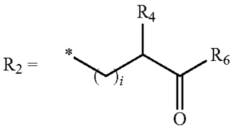

in which:

i=0 or 1;

$R_4$ represents a hydrogen atom or a radical $R_4$ chosen from the radicals (a1) to (a32) described below (a1)
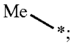
(a2)
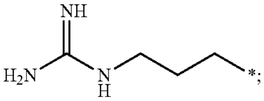
(a3)
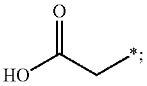
(a4)
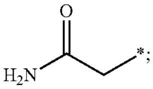
(a5)
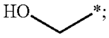
(a6)
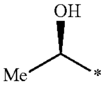
(a7)
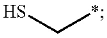
(a8)
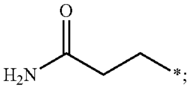
(a9)
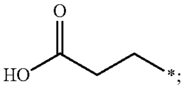
(a10)
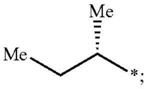
(a11)
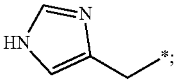
(a12)
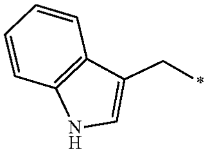
(a13)
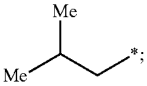
(a14)
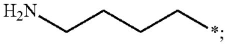
(a15)
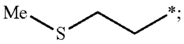
(a16)
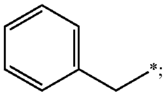
(a17)
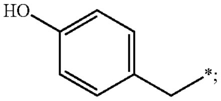
-continued
(a18)
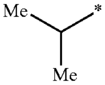
(a19)
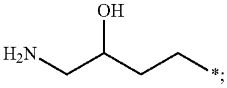
(a20)
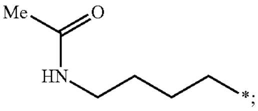
(a21)
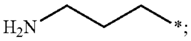
(a22)
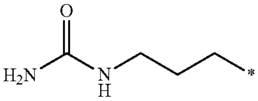
(a23)
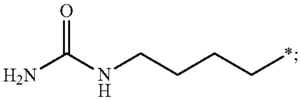
(a24)
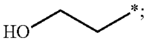
(a25)
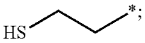
(a26)
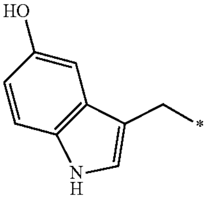
(a27)
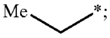
(a28)
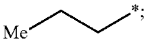
(a29)
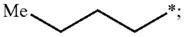
(a30)
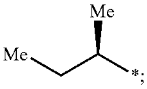
(a31)
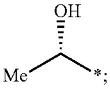
(a32)
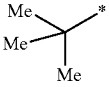
$R_4$ can also form, with $R_1$ and the nitrogen atom which bears $R_1$, a saturated heterocycle of formula A1 or A2 or A3:

A1

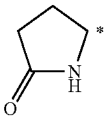

A2

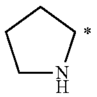

A3

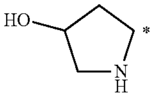

$R_6$ denotes i) a hydroxyl radical —OH;

ii) an alkoxide —$O^-$, $M^+$ with $M^+$ representing a cation such as zinc ($Zn^{2+}$), manganese ($Mn^{2+}$), copper ($Cu^{2+}$), iron ($Fe^{2+}$, $Fe^{3+}$), or an alkali metal cation such as $Na^+$ or $K^+$, or an alkaline-earth metal cation such as $Mg^{2+}$ or $Ca^{2+}$, or an ammonium cation;

iii) a saturated or unsaturated ($C_1$-$C_6$)alkoxy radical;

iv) a radical —$NR_fR_g$ with $R_f$ and $R_g$, which may be identical or different, representing a hydrogen atom or a ($C_1$-$C_6$)alkyl group.

or else $R_1$ and $R_2$ form, with the nitrogen atom to which they are attached, an optionally substituted heterocycloalkyl, such as piperazino, piperidino or morpholino.

$R_s$ represents a hydrogen atom or a methyl radical or an acetyl radical;

said radicals $R_s$ preferably all being identical and all preferably denoting a hydrogen atom or an acetyl radical;

$R'_s$ represents a radical chosen from a hydrogen atom or an acetyl radical.

More preferentially, the compounds of formula (I) are chosen from the compounds of formulae (I'), (I''), (I''''), (I'a), (I''a), (I''''a) and (I'b) below:

(I')

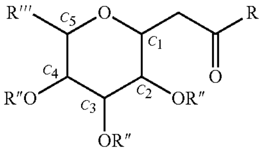

(I'')

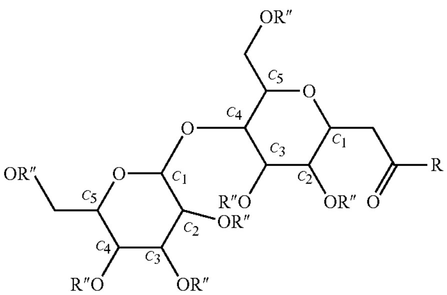

-continued (I'''')

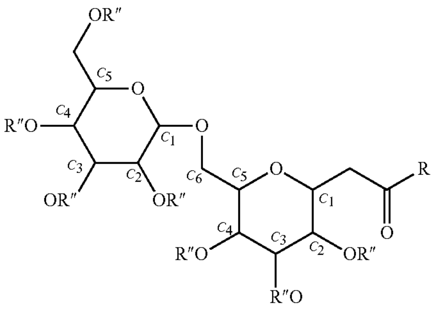

(I'a)

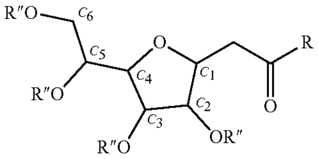

(I''a)

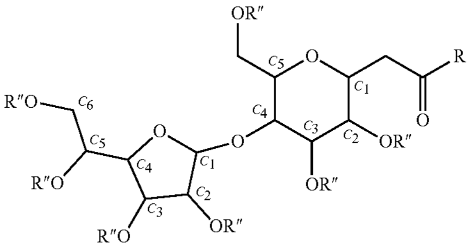

(I''''a)

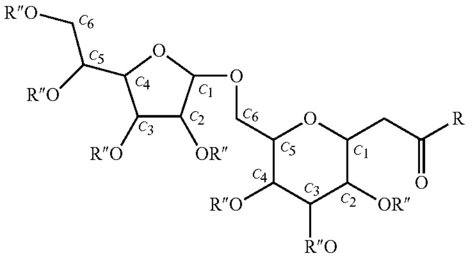

(I'b)

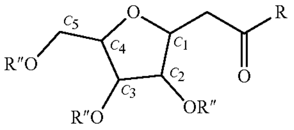

and also the solvates thereof such as hydrates, the optical and geometric isomers and tautomers thereof and the organic or mineral base or acid salts thereof, in which formulae (I'), (I''), (I''''), (I'a), (I''a), (I''''a) and (I'b):

R is as previously defined, and preferably represents one of the following groups:

i) hydroxyl; this hydroxyl can be in the form of an alkoxide $O^-$, $M^+$ with $M^+$ representing a cation such as zinc ($Zn^{2+}$), manganese ($Mn^{2+}$), copper ($Cu^{2+}$), iron ($Fe^{2+}$, $Fe^{3+}$), sodium ($Na^+$), potassium ($K^+$), magnesium ($Mg^{2+}$), calcium ($Ca^{2+}$), or ammonium; (when R is in the form of an alkoxide, it forms, with the carbonyl in the alpha position a carboxylate function $COO^-$, $M^+$ with $M^+$ as previously defined);

ii) ($C_1$-$C_{18}$)alkoxy; preferably $C_1$-$C_4$ alkoxy and more preferentially ethoxy;

iii) amino —$NR'_1R'_2$ with $R'_1$ and $R'_2$, independently of one another, representing:

for $R'_1$:

i) a hydrogen atom;

ii) a $(C_1\text{-}C_{18})$alkyl group, preferably $(C_1\text{-}C_6)$alkyl, preferentially a methyl;

for $R'_2$:

i) a hydrogen atom;

ii) a $(C_1\text{-}C_{18})$alkyl group;

iii) a radical such as:

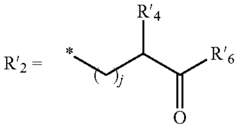

in which:

j=0 or 1;

$R'_4$ represents a hydrogen atom or $R'_4$ is chosen from the radicals (a1) to (a32) described below:

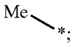
(a1)

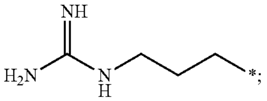
(a2)

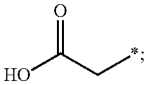
(a3)

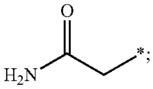
(a4)

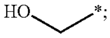
(a5)

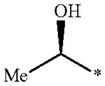
(a6)

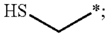
(a7)

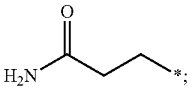
(a8)

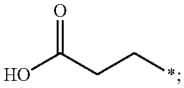
(a9)

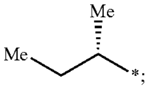
(a10)

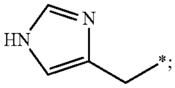
(a11)

-continued

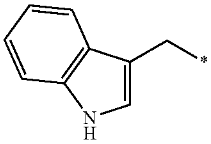
(a12)

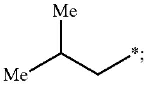
(a13)

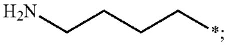
(a14)

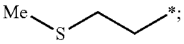
(a15)

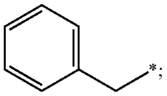
(a16)

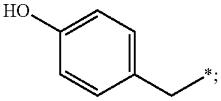
(a17)

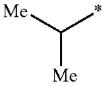
(a18)

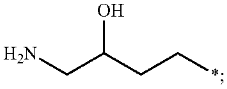
(a19)

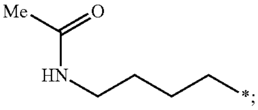
(a20)

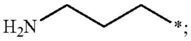
(a21)

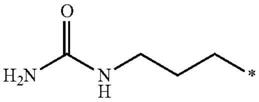
(a22)

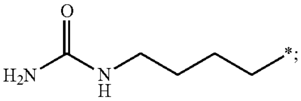
(a23)

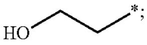
(a24)

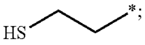
(a25)

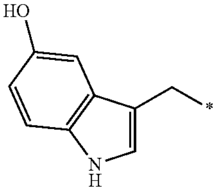
(a26)

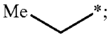
(a27)

-continued (a28)

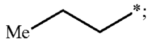

(a29)

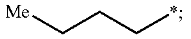

(a30)

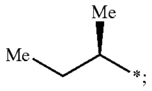

(a31)

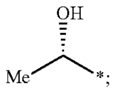

(a32)

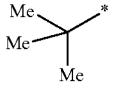

$R'_4$ can also form, with $R'_1$ and the nitrogen which bears $R'_1$, a saturated heterocycle of formula A1 or A2 or A3:

A1

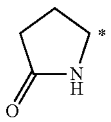

A2

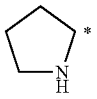

A3

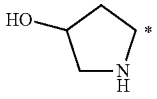

$R'_6$ denotes i) a hydroxyl radical —OH;

ii) an alkoxide $—O^-$, $M^+$ with $M^+$ representing a cation such as zinc ($Zn^{2+}$), manganese ($Mn^{2+}$), copper ($Cu^{2+}$), iron ($Fe^{2+}$, $Fe^{3+}$), or an alkali metal cation such as $Na^+$ or $K^+$, or an alkaline-earth metal cation such as $Mg^{2+}$ or $Ca^{2+}$, or an ammonium cation;

iii) a saturated or unsaturated $(C_1-C_6)$alkoxy radical;

iv) a radical $—NR_fR_g$ with $R_f$ and $R_g$, which may be identical or different, representing a hydrogen atom or a $(C_1-C_6)$alkyl group.

Furthermore preferably, $R'_6$ represents a hydroxyl radical, an alkoxide $—O^-$, $M^+$, a saturated $(C_1-C_6)$alkoxy radical, in particular methoxy or ethoxy, or an amino radical $NH_2$;

or else $R'_1$ and $R'_2$ form, with the nitrogen atom to which they are attached, an optionally substituted heterocycloalkyl, such as piperazino, piperidino or morpholino.

R" is as previously defined, and preferably represents a hydrogen atom or an acetyl radical, and preferably a hydrogen atom;

R'" represents a hydrogen atom, or a $(C_1-C_6)$alkyl group, or a $—CH_2—OR"$ group with R" as defined previously, in particular hydrogen or an acetyl radical, and preferably a hydrogen atom. Preferably, R'" represents a hydrogen atom, or a $(C_1-C_4)$alkyl group such as methyl, or a $—CH_2—OR"$ group with R" denoting a hydrogen atom or an acetyl radical.

According to one particular embodiment, the compounds of the invention are of formula (I'). By way of example of compounds of formula (I'), mention may be made of the compounds 2, 3 and 4 previously described, and also the salts, solvates and isomers thereof.

According to another particular embodiment of the invention, the compounds of the invention are of formula (I").

According to another particular embodiment of the invention, the compounds of the invention are of formula (I"").

According to another particular embodiment of the invention, the compounds of the invention are of formula (I'a).

According to another particular embodiment of the invention, the compounds of the invention are of formula (I"a).

According to another particular embodiment of the invention, the compounds of the invention are of formula (I""a).

According to another particular embodiment of the invention, the compounds of the invention are of formula (I'b). By way of example of a compound of formula (I'b), mention may be made of the compound 5 previously described, and also the salts, solvates and isomers thereof.

According to one particular embodiment, S* and S*' represent a monosaccharide chosen from glucose, galactose, mannose, xylose, lyxose, fucose, arabinose, rhamnose, ribose, deoxyribose, quinovose, fructose, sorbose, talose, threose, erythrose, N-acetylglucosamine, N-acetylgalactosamine, glucosamine and galactosamine.

In particular, S* and S*' represent a monosaccharide chosen from D-glucose, D-galactose, D-mannose, D-xylose, L-xylose, D-lyxose, L-lyxose, L-fucose, L-arabinose, D-arabinose, L-rhamnose, L-ribose, D-ribose, 2-deoxy-D-ribose, 2-deoxy-L-ribose, D-quinovose, D-fructose, L-sorbose, D-talose, D-threose, D-erythrose, L-threose, L-erythrose, N-acetyl-D-glucosamine, N-acetyl-D-galactosamine, D-glucosamine and D-galactosamine. Preferably, S denotes a monosaccharide chosen from D-glucose, D-galactose, D-mannose, D-xylose, D-lyxose, L-fucose, L-arabinose, L-rhamnose, D-ribose, 2-deoxy-D-ribose, D-quinovose, D-fructose, L-sorbose, D-talose, D-threose, D-erythrose, N-acetyl-D-glucosamine, N-acetyl-D-galactosamine, D-glucosamine and D-galactosamine.

Advantageously, S* and S*' represent a monosaccharide chosen from glucose, xylose, rhamnose, mannose and galactose or a disaccharide chosen from lactose, maltose and cellobiose. In particular, S* denotes a monosaccharide chosen from D-glucose, D-xylose, L-rhamnose, D-mannose and D-galactose or a disaccharide chosen from D-lactose, D-maltose and D-cellobiose.

Preferably, S* and S*' represent a sugar chosen from glucose, xylose, rhamnose and lactose. More particularly, S* and S*' denote a sugar chosen from D-glucose, D-xylose, L-rhamnose and D-lactose. Preferentially, S* and S*' denote glucose, rhamnose or xylose. In particular, S* and S*' denote D-glucose, L-rhamnose or D-xylose.

According to another particular embodiment, S* and S*" represent a polysaccharide and in particular a disaccharide chosen from lactose, maltulose, palatinose, lactulose, amygdalose, turanose, cellobiose, isomaltose, rutinose and maltose.

According to one particular embodiment, the radicals S* and S*" represent a polysaccharide and in particular a disaccharide chosen from D-lactose, maltulose, palatinose, lactulose, amygdalose, D-turanose, D-cellobiose, isomaltose, rutinose and D-maltose.

According to another particular embodiment, R represents an amino group —$NR'_1R'_2$ with $R'_1$ and $R'_2$, independently of one another, representing:

for $R'_1$: a hydrogen atom or a $(C_1\text{-}C_{18})$alkyl, preferably $(C_1\text{-}C_6)$alkyl, group, preferentially a methyl;

for $R'_2$: a radical such as:

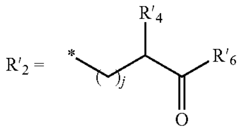

in which:

j=0 or 1; preferably j=0;

$R'_4$ represents a hydrogen atom when j=1, and in the other cases (that is to say when j=0) $R'_4$ is chosen from the radicals described below:

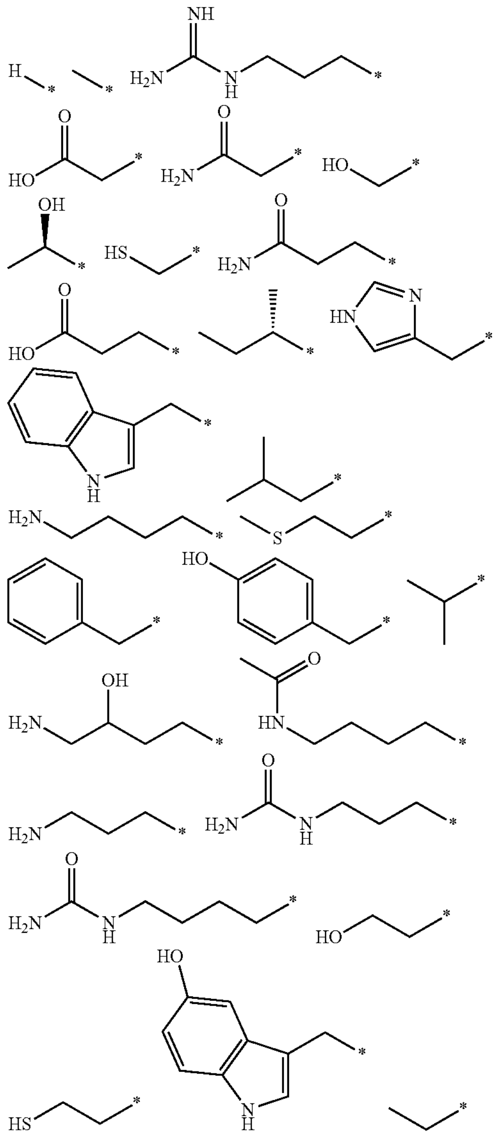

-continued

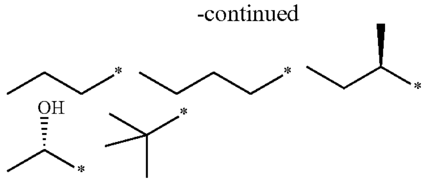

$R'_4$ can also form, with $R'_1$ and the nitrogen which bears $R'_1$, an alipsaturated heterocycle of formula A1 or A2 or A3:

A1

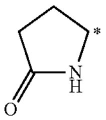

A2

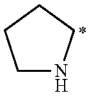

A3

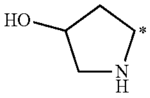

$R'_6$ denotes i) a hydroxyl radical —OH;

ii) an alkoxide —$O^-$, $M^+$ with $M^+$ representing a cation such as zinc ($Zn^{2+}$), manganese ($Mn^{2+}$), copper ($Cu^{2+}$), iron ($Fe^{2+}$, $Fe^{3+}$), or an alkali metal cation such as $Na^+$ or $K^+$, or an alkaline-earth metal cation such as $Mg^{2+}$ or $Ca^{2+}$, or an ammonium cation;

iii) a saturated $(C_1\text{-}C_6)$alkoxy radical, preferably methoxy or ethoxy;

iv) an amino radical —$NH_2$.

According to another particular embodiment, R represents an amino group —$NR'_1R'_2$ with $R'_1$ and $R'_2$, independently of one another, representing:

for $R'_1$: a hydrogen atom or a $(C_1\text{-}C_{10})$alkyl, preferably $(C_1\text{-}C_6)$alkyl, group, preferentially a methyl;

for $R'_2$: a hydrogen atom or a $(C_1\text{-}C_{16})$alkyl group, preferentially a methyl or an n-tetradecyl;

R" is as previously defined, and preferably represents a hydrogen atom or an acetyl radical, and preferably a hydrogen atom;

R'" represents a hydrogen atom, or a $(C_1\text{-}C_6)$alkyl group, or a —$CH_2$—OR" group with R" as defined previously, in particular hydrogen or an acetyl radical, and preferably a hydrogen atom. Preferably, R'" represents a hydrogen atom, or a $(C_1$—$C)$alkyl group such as methyl, or a —$CH_2$—OR" group with R" denoting a hydrogen atom or an acetyl radical.

According to this embodiment, according to a first variant, $R'_1$ and $R'_2$ are identical.

According to a second variant of this embodiment, $R'_1$ and $R'_2$ are different and preferably $R'_1$ denotes a hydrogen atom.

According to another particular embodiment, R represents a hydroxyl group; this hydroxyl can be in the form of an alkoxide $O^-$, $M^+$ with $M^+$ representing a cation such as zinc ($Zn^{2+}$), manganese ($Mn^{2+}$), copper ($Cu^{2+}$), iron ($Fe^{2+}$, $Fe^{3+}$), sodium ($Na^+$), potassium ($K^-$), magnesium ($Mg^{2+}$), calcium ($Ca^{2+}$), or ammonium; (when R is in the form of an alkoxide, it forms, with the carbonyl in the alpha position a carboxylate function $COO^-$, $M^+$ with $M^+$ as previously defined);

R" is as previously defined, and preferably represents a hydrogen atom or an acetyl radical, and preferably a hydrogen atom;

R'" represents a hydrogen atom, or a $(C_1-C_6)$alkyl group, or a —$CH_2$—OR" group with R" as defined previously, in particular hydrogen or an acetyl radical, and preferably a hydrogen atom. Preferably, R'" represents a hydrogen atom, or a $(C_1-C)$alkyl group such as methyl, or a —$CH_2$—OR" group with R" denoting a hydrogen atom or an acetyl radical.

A subject of the invention is also the novel compounds of formula (IIa), and also the solvates and/or isomers and/or salts thereof for which:

(IIa)

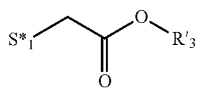

with:

$S^*_1$ denoting a monosaccharide sugar radical chosen from: D-glucose, D-galactose, D-mannose, D-xylose, D-lyxose, L-fucose, L-arabinose, D-arabinose, L-rhamnose, D-quinovose, D-fructose, L-sorbose, D-talose, N-acetyl-D-glucosamine, N-acetyl-D-galactosamine, D-glucosamine and D-galactosamine;

the saccharide unit comprising one or more hydroxyl groups optionally substituted with a radical $R'_a$ chosen from:

i) $(C_1-C_6)$alkyl; or ii) an acetyl radical;

said monosaccharide radical not being able to comprise a (hemi)acetal or (hemi)aminal function;

said monosaccharide radical being connected to the rest of the molecule by a bond between the $C_1$ carbon atom of said monosaccharide radical, this bond possibly being α or β anomeric;

$R'_3$ represents a group chosen from:

i) a hydrogen atom; ii) saturated or unsaturated $(C_1-C_{18})$ alkyl;

iii) optionally substituted aryl such as phenyl;

iv) optionally substituted aryl$(C_1-C_6)$alkyl, such as benzyl;

it being understood that:

when $S^*_1$ denotes a D-glucose, $R'_3$ cannot be a methyl or an ethyl, and $R'_3$ is other than a hydrogen atom when all its hydroxyl groups are substituted with an acetyl group ($R'_a$=acetyl);

when $S^*_1$ denotes a D-xylose, $R'_3$ cannot be a methyl or a $(C_{15}-C_{18})$alkyl;

when $S^*_1$ denotes a D-galactose, $R'_3$ cannot be a hydrogen, and $R'_3$ is other than a methyl or ethyl when all its hydroxyl groups are substituted with an acetyl group ($R'_a$=acetyl);

when $S^*_1$ denotes a D-mannose, $R'_3$ cannot be a hydrogen or a methyl;

when $S^*_1$ denotes an L-rhamnose, $R'_3$ is other than a hydrogen atom or than a methyl group when all its hydroxyl groups are substituted with an acetyl group ($R'_a$=acetyl);

when $S^*_1$ denotes an L-fucose, $R'_3$ cannot be a hydrogen;

when $S^*_1$ denotes a D-arabinose, $R'_3$ cannot be a methyl;

when $S^*_1$ denotes a D-talose, $R'_3$ is other than a hydrogen atom when all its hydroxyl groups are substituted with an acetyl group ($R'_a$=acetyl);

when $S^*_1$ denotes an N-acetyl-D-glucosamine, $R'_3$ cannot be an ethyl, and $R'_3$ is other than a hydrogen atom when all its hydroxyl groups are substituted with an acetyl group ($R'_a$=acetyl);

the compounds of formula (IIa) have a molar mass of less than 800 Da and do not comprise more than 3 rings in total.

When $R'_3$ denotes a hydrogen atom, as previously mentioned, the corresponding compounds of formula (IIa) may be in the form of salts (carboxylates $COO^-$, $M^+$, with $M^+$ having the definition previously mentioned).

Preferably, $S^*_1$ denotes a sugar chosen from D-glucose or D-xylose, more preferentially D-glucose.

Preferably, the hydroxyl groups of $S^*_1$ are not substituted.

Preferably, $R'_3$ represents a hydrogen atom or a $(C_1-C_{18})$ alkyl group, which is preferably saturated, and more preferentially a $C_2-C_6$ alkyl group, in particular ethyl.

Among the compounds of formula (IIa), mention may in particular be made of the compound 2 (and/or solvates thereof and/or salts thereof):

compound 2

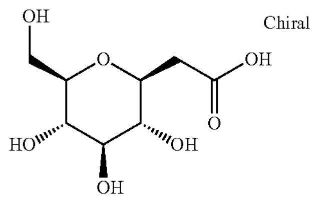

$S^*_1$ = D-glucose

A subject of the invention is also the novel compounds of formula (IIb), and also the solvates and/or isomers and/or salts thereof:

(IIb)

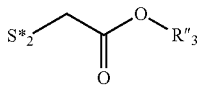

with:

$S^*_2$ denoting a monosaccharide sugar radical or denotes a polysaccharide sugar radical comprising 2 saccharide units, each saccharide unit (the saccharide unit in the case of a monosaccharide or each saccharide unit in the case of polysaccharides) comprising one or more hydroxyl groups optionally substituted with a radical $R'_b$ chosen from:

i) $(C_1-C_6)$alkyl; or ii) an acetyl radical;

said monosaccharide or polysaccharide radical not being able to comprise a (hemi)acetal or (hemi) aminal function;

said monosaccharide or polysaccharide radical possibly also comprising one or more amino groups $NR_bR_c$ with $R_b$ and $R_c$, which may be identical or different, representing a hydrogen atom, or an acetyl group, or a protective group for the amino function, such as $(C_2-C_6)$alkyl(thio)carbonyl;

said monosaccharide or polysaccharide radical being connected to the rest of the molecule by a bond between the $C_1$ carbon atom of one of the sugars of said monosaccharide or polysaccharide radical, this bond possibly being α or β anomeric;

R"$_3$ represents a group chosen from:

i) a hydrogen atom; ii) saturated or unsaturated ($C_2$-$C_{14}$) alkyl;

it being understood that:

when S*$_2$ denotes a monosaccharide, R"$_3$ cannot be a hydrogen or an ethyl;

when S*$_2$ denotes a monosaccharide in the pyranose form, R"$_3$ cannot be an n-butyl;

the compounds of formula (IIb) have a molar mass of less than 800 Da and do not comprise more than 3 rings in total.

When R'$_3$ denotes a hydrogen atom, as previously mentioned, the corresponding compounds of formula (IIb) may be in the form of salts (carboxylates $COO^-$, $M^+$, with $M^+$ having the definition previously mentioned).

According to a particular form of the invention, S*2 denotes a monosaccharide as defined previously with the exception of D-glucose, D-galactose, D-mannose, D-xylose, D-lyxose, L-fucose, L-arabinose, D-arabinose, L-rhamnose, D-quinovose, D-fructose, L-sorbose, D-talose, N-acetyl-D-glucosamine, N-acetyl-D-galactosamine, D-glucosamine and D-galactosamine.

When S*$_2$ denotes a disaccharide, it is preferably from the following disaccharides: lactose, maltulose, palatinose, lactulose, amygdalose, turanose, cellobiose, isomaltose, rutinose and maltose. More preferentially, it is D-lactose, D-maltose or D-cellobiose.

Preferably, the hydroxyl groups of S*$_2$ are not substituted.

Preferably, R"$_3$ represents a hydrogen atom or a ($C_2$-$C_6$) alkyl group, which is preferably saturated, in particular ethyl.

A subject of the invention is also the novel compounds of formula (IIc), and also the solvates and/or isomers and/or salts thereof:

(IIc)

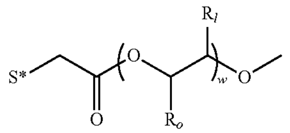

in which S*, $R_l$, $R_o$ and w are as previously defined.

S* denotes a monosaccharide sugar radical or denotes a polysaccharide sugar radical comprising from 2 to 5 saccharide units, preferably from 2 to 3 saccharide units, each saccharide unit (the saccharide unit in the case of a monosaccharide or each saccharide unit in the case of polysaccharides) comprising one or more hydroxyl groups optionally substituted with a radical R' chosen from:

i) ($C_1$-$C_6$)alkyl; or ii) an acetyl radical;

said monosaccharide or polysaccharide radical not being able to comprise a (hemi)acetal or (hemi) aminal function;

said monosaccharide or polysaccharide radical possibly also comprising one or more amino groups $NR_bR_c$ with $R_b$ and $R_c$, which may be identical or different, representing a hydrogen atom, or an acetyl group, or a protective group for the amino function, such as ($C_2$-$C_6$)alkyl(thio)carbonyl;

said monosaccharide or polysaccharide radical being connected to the rest of the molecule by a bond between the $C_1$ carbon atom of one of the sugars of said monosaccharide or polysaccharide radical, this bond possibly being α or β anomeric;

$R_l$ and $R_o$, independently of one another, denote a hydrogen atom or a methyl radical, it being understood that $R_l$ and $R_o$ cannot simultaneously denote a methyl radical;

w=1 to 10, limits included, it being understood that:

the compounds of formula (IIc) have a molar mass of less than 800 Da and do not comprise more than 3 rings in total.

Preferably, the hydroxyl groups of S* are not substituted and the optional amino groups are free (—$NH_2$) or all substituted with an acetyl group (—CO—$CH_3$) ($R_b$=H and $R_c$=H or acetyl).

Preferably, w is between 1 and 5, more preferentially between 1 and 3.

A subject of the invention is also the novel compounds of formula (IIIa), and also the solvates and/or isomers and/or salts thereof for which:

(IIIa)

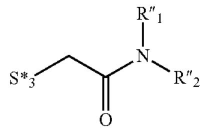

with:

S*$_3$ denoting a monosaccharide sugar radical chosen from: D-xylose, D-fructose, L-sorbose, N-acetyl-D-glucosamine, N-acetyl-D-galactosamine, D-glucosamine, D-galactosamine and in particular D-xylose;

the saccharide unit comprising one or more hydroxyl groups optionally substituted with a radical R'$_c$ chosen from:

i) ($C_1$-$C_6$)alkyl; or ii) an acetyl radical;

said monosaccharide radical not being able to comprise a (hemi)acetal or (hemi)aminal function;

said monosaccharide radical being connected to the rest of the molecule by a bond between the $C_1$ carbon atom of said monosaccharide radical, this bond possibly being α or β anomeric;

R"$_1$ represents a group chosen from:

i) a hydrogen atom;

ii) a ($C_1$-$C_{18}$)alkyl group;

iii) a ($C_2$-$C_{18}$)alkenyl group;

R"$_2$ represents a group chosen from:

i) a hydrogen atom;

ii) a ($C_1$-$C_{18}$)alkyl group;

iii) a ($C_2$-$C_{18}$)alkenyl group;

iv) an aryl($C_1$-$C_4$)alkyl group optionally substituted in particular with at least one hydroxyl and/or saturated or unsaturated ($C_1$-$C_4$)alkoxy group;

v) an optionally substituted aryl or heteroaryl radical;

or else R"$_1$ and R"$_2$ form, with the nitrogen atom to which they are attached, an optionally substituted heterocycloalkyl, such as piperazino, piperidino or morpholino, it being understood that:

the compounds of formula (IIIa) have a molar mass of less than 800 Da and do not comprise more than 3 rings in total.

Preferably, $S^*_3$ denotes D-xylose.

Preferably, the hydroxyl groups of $S^*_3$ are not substituted.

Preferably, $R''_1$ denotes a hydrogen atom or a $C_1$-$C_4$ alkyl group, such as in particular a methyl group. Preferentially, $R''_2$ denotes a hydrogen atom or a $C_1$-$C_{16}$ alkyl group such as in particular a methyl or n-tetradecyl group.

Among the compounds of formula (IIIa), the novel compounds 3 and 5 (and/or solvates thereof and/or salts thereof) is more particularly preferred:

compound 3

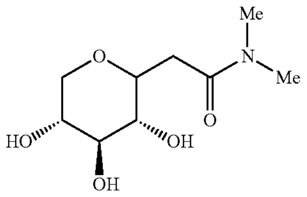

$S^*_3$ = D-xylose compound 5

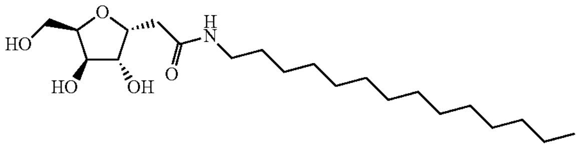

$S^*_3$ = D-xylo-furanose

A subject of the invention is also the novel compounds of formula (IIIb), and also the solvates and/or isomers and/or salts thereof for which:

(IIIb)

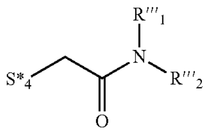

with:

$S^*_4$ denoting a monosaccharide sugar radical or denotes a polysaccharide sugar radical comprising from 2 to 5 saccharide units, preferably from 2 to 3 saccharide units, each saccharide unit (the saccharide unit in the case of a monosaccharide or each saccharide unit in the case of polysaccharides) comprising one or more hydroxyl groups optionally substituted with a radical $R'_d$ chosen from:

i) ($C_1$-$C_6$)alkyl; or ii) an acetyl radical;

said monosaccharide or polysaccharide radical not being able to comprise a (hemi)acetal or (hemi) aminal function;

said monosaccharide or polysaccharide radical possibly also comprising one or more amino groups $NR_bR_c$ with $R_b$ and $R_c$, which may be identical or different, representing a hydrogen atom, or an acetyl group, or a protective group for the amino function, such as ($C_2$-$C_6$)alkyl(thio)carbonyl; with the exclusion of the monosaccharides of 5-aminofuranose type;

said monosaccharide or polysaccharide radical being connected to the rest of the molecule by a bond between the $C_1$ carbon atom of one of the sugars of said monosaccharide radical, this bond possibly being α or β anomeric;

$R'''_1$ represents a group chosen from:

i) a hydrogen atom;

ii) a ($C_1$-$C_{18}$)alkyl group;

iii) a ($C_2$-$C_{18}$)alkenyl group;

$R'''_2$ represents a group chosen from:

i) a ($C_1$-$C_{18}$)alkyl group; or ii) a ($C_2$-$C_{18}$)alkenyl group;

iii) an aryl($C_1$-$C_4$)alkyl group optionally substituted in particular with at least one hydroxyl and/or saturated or unsaturated ($C_1$-$C_4$)alkoxy group;

iv) an optionally substituted aryl or heteroaryl radical;

or else $R'''_1$ and $R'''_2$ form, with the nitrogen atom to which they are attached, an optionally substituted heterocycloalkyl, such as piperazino or morpholino; the piperidine ring is excluded;

it being understood that, in the case where $R'''_1$ represents a hydrogen atom:

when $S^*_4$ denotes a D-galactose, $R'''_2$ cannot be an alkyl or alkenyl group;

when $S^*_4$ denotes a monosaccharide, $R'''_2$ cannot be a substituted or unsubstituted benzyl group;

when $S^*_4$ denotes a monosaccharide of pyranose type, $R'''_2$ cannot be a substituted or unsubstituted phenyl group or a 2-benzothiazolyl group or a 2-benzimidazolyl group;

it being understood that:

the compounds of formula (IIIb) have a molar mass of less than 800 Da and do not comprise more than 3 rings in total; and that the following compound is excluded:

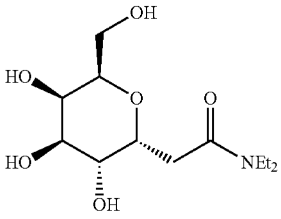

[261724-24-7] IN
D-glycero-L-gluco-Octonamide,
3,7-anhydro-2-deoxy-N,N-diethyl-

When $S^*_4$ denotes a monosaccharide, said monosaccharide is other than D-xylose, D-fructose, L-sorbose, N-acetyl-D-glucosamine, N-acetyl-D-galactosamine, D-glucosamine, D-galactosamine.

When $S^*_4$ denotes a disaccharide, it is preferably from the following disaccharides: lactose, maltulose, palatinose, lactulose, amygdalose, turanose, cellobiose, isomaltose, rutinose and maltose. More preferentially, it is D-lactose, D-maltose or D-cellobiose.

Preferably, the hydroxyl groups of $S^*_4$ are not substituted.

Preferably, $R'''_1$ denotes a hydrogen atom or a $C_1$-$C_4$ alkyl group, such as in particular a methyl radical. Preferentially, $R'''_1$ denotes a methyl group. Preferably, $R'''_2$ denotes a hydrogen atom or a $C_1$-$C_4$ alkyl group such as in particular a methyl radical.

Among the compounds of formula (IIIb), mention may in particular be made of the novel compound 4 (and/or solvates thereof and/or salts thereof):

compound 4

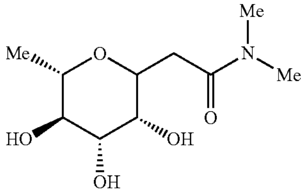

$S^*_4$ = L-rhamnose

A subject of the invention is also the novel compounds of formula (IIIc), and also the solvates and/or isomers and/or salts thereof for which:

(IIIc)

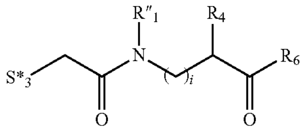

with:

$S^*_3$ denoting a monosaccharide sugar radical chosen from: D-xylose, D-fructose, L-sorbose, N-acetyl-D-glucosamine, N-acetyl-D-galactosamine, D-glucosamine and D-galactosamine;

the saccharide unit comprising one or more hydroxyl groups optionally substituted with a radical $R'_c$ chosen from:

i) $(C_1-C_6)$alkyl; or ii) an acetyl radical;

said monosaccharide radical not being able to comprise a (hemi)acetal or (hemi)aminal function;

said monosaccharide radical being connected to the rest of the molecule by a bond between the $C_1$ carbon atom of one of the sugars of said monosaccharide radical, this bond possibly being α or β anomeric;

$R''_1$ represents a group chosen from:

i) a hydrogen atom;

ii) a $(C_1-C_{18})$alkyl group;

iii) a $(C_2-C_{18})$alkenyl group;

i=0 or 1;

$R_4$ represents a hydrogen atom or $R_4$ is chosen from the radicals (a1) to (a32) described below:

(a1)

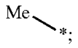

(a2)

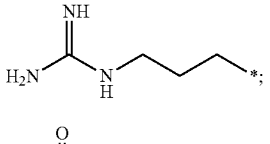

(a3)

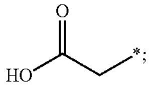

(a4)

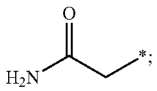

(a5)

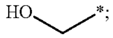

-continued (a6)

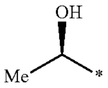

(a7)

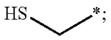

(a8)

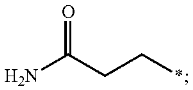

(a9)

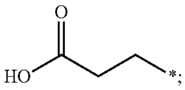

(a10)

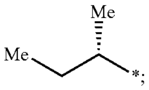

(a11)

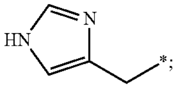

(a12)

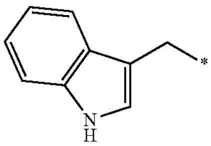

(a13)

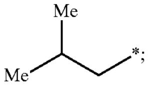

(a14)

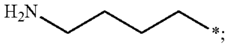

(a15)

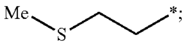

(a16)

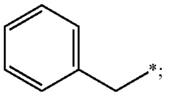

(a17)

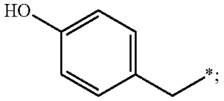

(a18)

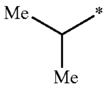

(a19)

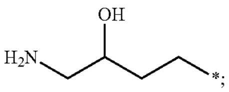

(a20)

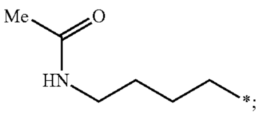

(a21)

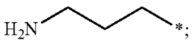

-continued (a22)

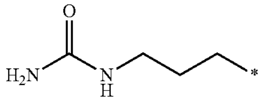

(a23)

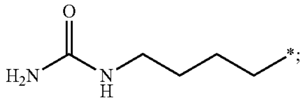

(a24)

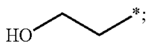

(a25)

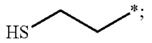

(a26)

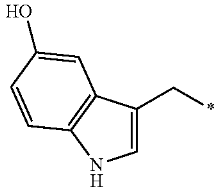

(a27)

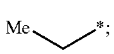

(a28)

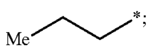

(a29)

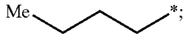

(a30)

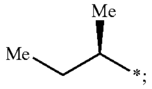

(a31)

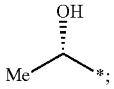

(a32)

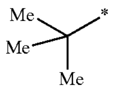

$R_4$ can also form, with $R''_1$ and the nitrogen atom which bears $R''_1$, a saturated heterocycle of formula A or A2 or A3:

A1

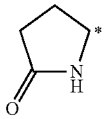

A2

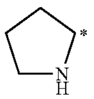

A3

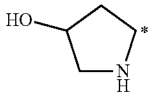

$R_6$ denotes i) a hydroxyl radical —OH;

ii) an alkoxide $—O^-$, $M^+$ with $M^+$ representing a cation such as zinc ($Zn^{2+}$), manganese ($Mn^{2+}$), copper ($Cu^{2+}$), iron ($Fe^{2+}$, $Fe^{3+}$), or an alkali metal cation such as $Na^+$ or $K^+$, or an alkaline-earth metal cation such as $M^{2+}$ or $Ca^{2+}$, or an ammonium cation;

iii) a saturated or unsaturated ($C_1$-$C_6$)alkoxy radical;

iv) a radical $—NR_fR_g$ with $R_f$ and $R_g$, which may be identical or different, representing a hydrogen atom or a ($C_1$-$C_6$)alkyl group.

It being understood that the compounds of formula (IIIc) have a molar mass of less than 800 Da and do not comprise more than 3 rings in total.

Preferably, the hydroxyl groups of $S^*_3$ are not substituted.

Preferably, $R''_1$ denotes a hydrogen atom or a $C_1$-$C_4$ alkyl group, such as in particular a methyl radical. Preferentially, $R''_1$ denotes a hydrogen atom.

Preferably, $R_6$ denotes a hydroxyl, ethoxy or $NH_2$ group.

When $R_6$ denotes a hydrogen atom, the corresponding compounds of formula (IIIc) can of course be in the form of salts (carboxylate).

Preferably, i=0 and $R_4$ represents a hydrogen atom or a radical chosen from the radicals (a1) or (a5) or (a16) below:

(a1)

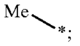

(a5)

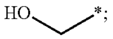

(a16)

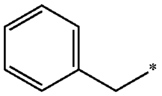

A subject of the invention is also the novel compounds of formula (IIId), and also the solvates and/or isomers and/or salts thereof:

(IIId)

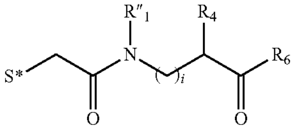

with:

S* denoting a monosaccharide sugar radical or denotes a polysaccharide sugar radical comprising from 2 to 5 saccharide units, preferably from 2 to 3 saccharide units, each saccharide unit (the saccharide unit in the case of a monosaccharide or each saccharide unit in the case of polysaccharides) comprising one or more hydroxyl groups optionally substituted with a radical R' chosen from:

i) ($C_1$-$C_6$)alkyl; or ii) an acetyl radical;

said monosaccharide or polysaccharide radical not being able to comprise a (hemi)acetal or (hemi) aminal function;

said monosaccharide or polysaccharide radical possibly also comprising one or more amino groups $NR_bR_c$ with $R_b$ and $R_c$, which may be identical or different, representing a hydrogen atom, or an acetyl group, or a protective group for the amino function, such as ($C_2$-$C_6$)alkyl(thio)carbonyl;

said monosaccharide or polysaccharide radical being connected to the rest of the molecule by a bond between the $C_1$ carbon atom of one of the sugars of said monosaccharide or polysaccharide radical, this bond possibly being α or β anomeric;

R"$_1$ represents a group chosen from:

i) a hydrogen atom;

ii) a ($C_1$-$C_{18}$)alkyl group;

iii) a ($C_2$-$C_{18}$)alkenyl group;

i=0 or 1;

$R_4$ represents a hydrogen atom or $R_4$ is chosen from the radicals (a1) to (a32) described below:

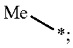
(a1)

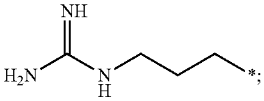
(a2)

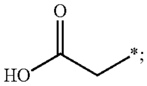
(a3)

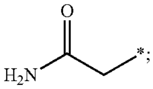
(a4)

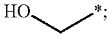
(a5)

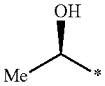
(a6)

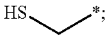
(a7)

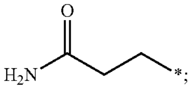
(a8)

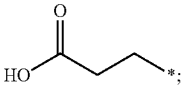
(a9)

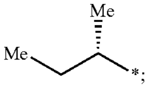
(a10)

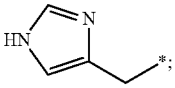
(a11)

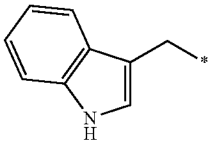
(a12)

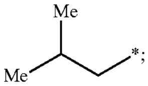
(a13)

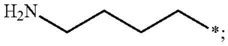
(a14)

-continued

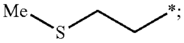
(a15)

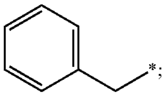
(a16)

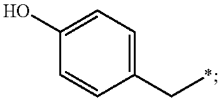
(a17)

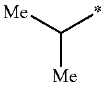
(a18)

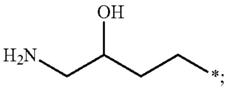
(a19)

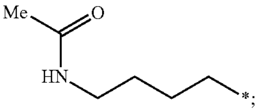
(a20)

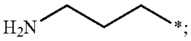
(a21)

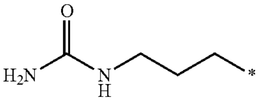
(a22)

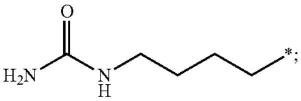
(a23)

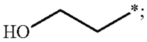
(a24)

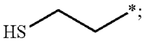
(a25)

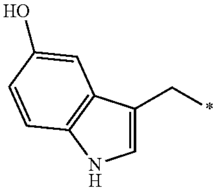
(a26)

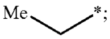
(a27)

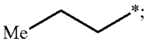
(a28)

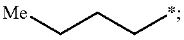
(a29)

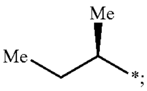
(a30)

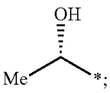
(a31)

-continued (a32)

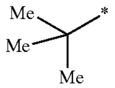

$R_4$ can also form, with $R''_1$ and the nitrogen atom which bears $R''_1$, a saturated heterocycle of formula A1 or A2 or A3:

A1

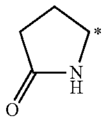

A2

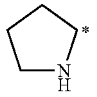

A3

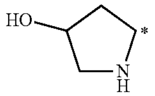

$R_6$ denotes

- i) a hydroxyl radical —OH;
- ii) an alkoxide $—O^-$, $M^+$ with $M^+$ representing a cation such as zinc ($Zn^{2+}$), manganese ($Mn^{2+}$), copper ($Cu^{2+}$), iron ($Fe^{2+}$, $Fe^{3+}$), or an alkali metal cation such as $Na^+$ or $K^+$, or an alkaline-earth metal cation such as $Mg^{2+}$ or $Ca^{2+}$, or an ammonium cation;
- iii) a saturated or unsaturated $(C_1\text{-}C_6)$alkoxy radical;
- iv) a radical $—NR_fR_g$ with $R_f$ and $R_g$, which may be identical or different, representing a hydrogen atom or a $(C_1\text{-}C_6)$alkyl group.

It being understood that: in the case where $R''_1$ represents a hydrogen atom and when S* denotes a monosaccharide of pyranose type, $R_6$ cannot be a methyl or a hydroxyl group; it being understood that:

the compounds of formula (IIId) have a molar mass of less than 800 Da and do not comprise more than 3 rings in total; and that the following compound is excluded:

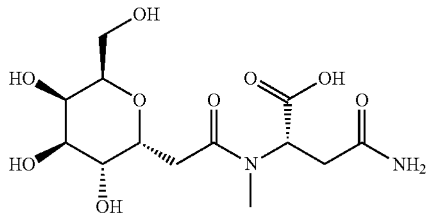

[1000184-29-1]
IN L-Asparagine, N2-(3,7-anhydro-2-deoxy-D-glycero-L-gluco-octonoyl)-N2-methyl- Preferably, the hydroxyl groups of S* are not substituted.

Preferably, $R''_1$ denotes a hydrogen atom or a $C_1\text{-}C_4$ alkyl group, such as in particular a methyl radical. Preferentially, $R''_1$ denotes a hydrogen atom.

Preferably, $R_6$ denotes a hydroxyl, ethoxy or $NH_2$ group.

When $R''_6$ denotes a hydroxyl group, the corresponding compounds of formula (IIId) can of course be in the form of salts (carboxylates).

Preferably, i=0 and $R_4$ represents a hydrogen atom or a radical chosen from the radicals (a1) or (a5) or (a16) below:

(a1)

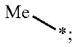

(a5)

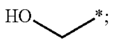

(a16)

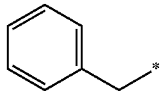

A subject of the invention is also the novel compounds of formula (IIIe), and also the solvates and/or isomers and/or salts thereof for which:

(IIIe)

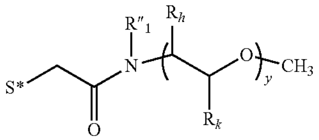

S* denotes a monosaccharide sugar radical or denotes a polysaccharide sugar radical comprising from 2 to 5 saccharide units, preferably from 2 to 3 saccharide units, each saccharide unit (the saccharide unit in the case of a monosaccharide or each saccharide unit in the case of polysaccharides) comprising one or more hydroxyl groups optionally substituted with a radical R' chosen from:

- i) $(C_1\text{-}C_6)$alkyl; or
- ii) an acetyl radical;

said monosaccharide or polysaccharide radical not being able to comprise a (hemi)acetal or (hemi) aminal function;

said monosaccharide or polysaccharide radical possibly also comprising one or more amino groups $NR_bR_c$ with $R_b$ and $R_c$, which may be identical or different, representing a hydrogen atom, or an acetyl group, or a protective group for the amino function, such as $(C_2\text{-}C_6)$alkyl(thio)carbonyl;

said monosaccharide or polysaccharide radical being connected to the rest of the molecule by a bond between the $C_1$ carbon atom of one of the sugars of said monosaccharide or polysaccharide radical, this bond possibly being α or β anomeric;

$R''_1$ represents a group chosen from:

- i) a hydrogen atom;
- ii) a $(C_1\text{-}C_{18})$alkyl group;
- iii) a $(C_2\text{-}C_{18})$alkenyl group;

$R_h$ and $R_k$, independently of one another, denote a hydrogen atom or a methyl radical, it being understood that $R_h$ and $R_k$ cannot simultaneously denote a methyl radical;

y=1 to 10, limits included;

it being understood that the compounds of formula (IIIe) have a molar mass of less than 800 Da and do not comprise more than 3 rings in total.

Preferably, the hydroxyl groups of S* are not substituted and the optional amino groups are free ($—NH_2$) or substituted with an acetyl group ($—CO—CH_3$) ($R_b$=H and $R_c$=H or acetyl).

Preferably, y is between 1 and 5, more preferentially between 1 and 3.

The preferred novel compounds are the compounds 1 to 5 previously described.

Process for Preparing the Compounds of Formula (I), in Particular the Compounds of Formulae (IIa), (IIb), (IIc), (IIIa), (IIIb), (IIIc), (IIId) and/or (IIIe), of the Invention Another subject of the invention is the process for preparing, or a process for the chemical synthesis of, the compounds of formula (I) as previously defined for which A is other than a hydrogen atom, on the one hand, and of the compounds of formula (I) for which A denotes a hydrogen atom and the sugar S* is a monosaccharide in pyranose or furanose form, on the other hand, according to scheme (1) described below.

The compounds of formula ($II^1$) comprise certain compounds (carboxylic acids) of formulae (IIa) and (IIb). The compounds of formula ($II^2$) comprise certain compounds (esters) of formulae (IIa) and (IIb), and also the compounds of formula (IIc).

The compounds of formula ($III^1$) comprise the compounds of formulae (IIIa), (IIIb), (IIIc), (IIId) and (IIIe).

The novel compounds of formulae ($II^1$), ($II^2$) and ($III^1$) can be prepared according to the following scheme (1):

Scheme (1)

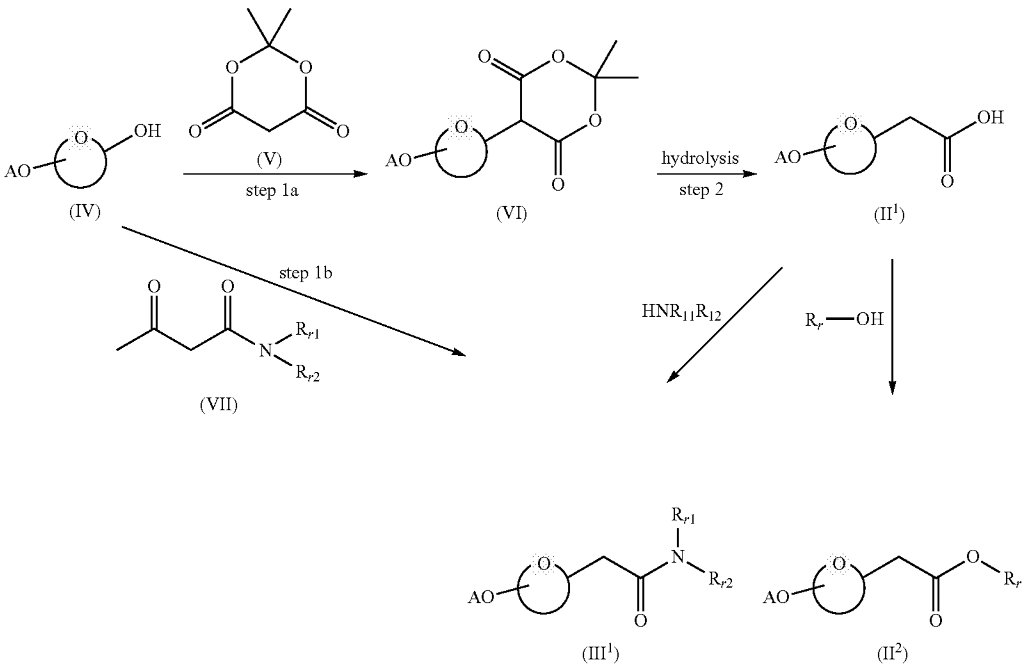

According to this scheme, if, in compound (IV), A denotes a hydrogen atom, the synthetic step 1a must be preceded by a step of protecting the radicals AO=OH of the sugar. In this case, compounds ($II^1$), ($II^2$) and also compounds ($III^1$) obtained via ($II^1$) are obtained in the form of protected sugars (A other than H) and the corresponding compounds ($II^1$), ($II^2$), ($III^1$) for which A=H are obtained after a deprotection step.

The compounds ($III^1$) may also be obtained by reaction of a protected or unprotected compound (IV) (A=H or other than H) with a beta-keto amide (VII) according to step 1b. If (IV) is such that A=H, then, in this case, ($III^1$) is such that A=H. If (IV) is such that A is other than H, then ($III^1$) is such that A is other than H and compound ($III^1$) for which A=H is obtained after a step of deprotection of the hydroxyls of the sugar.

The synthetic route described in scheme (1) comprises the following steps:

Step 1a consists in reacting a monosaccharide or a polysaccharide of formula (IV) with Meldrum's acid (V), in particular in the presence of an organic base such as a tertiary amine, for instance triethylamine or diisopropylethylamine.

(IV)

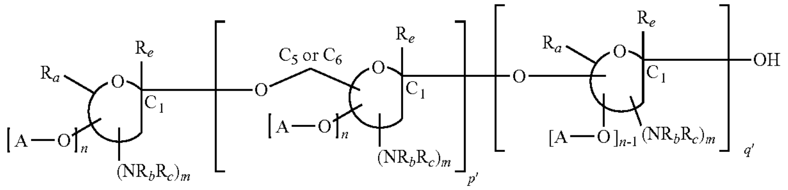

(IV)

In which formula (IV), A, $R_a$, $R_b$, $R_c$, $R_e$, n, and m are as previously defined, p' and q' representing an integer inclusively between 0 and 4, with p'+q' inclusively between 0 and 4, in particular between 0 and 2, preferably p'+q'=0 or 1, it being understood that the two units between square brackets can be reversed; the compound of formula (IV) being represented in the scheme by:

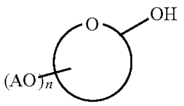

step 1 being carried out in particular in a non-protic polar solvent such as DMF or acetonitrile, by heating optionally at a temperature between 30° C. and 100° C., in particular at 40-50° C., preferably for a period of between 1 h and 7 days, in particular between 2 and 7 days, such as 2 days, so as to give the compound comprising sugar unit (VI).

Step 2 consists in carrying out a hydrolysis of the compound (VI), in particular in acid medium, and in particular in the presence of a weak organic acid such as acetic acid, which can also serve as solvent, or else in acid medium diluted in aqueous solution, such as hydrochloric acid, in a protic polar solvent such as water, by optionally heating at a temperature of formula ($II^2$) by esterification, or with an amine $R_{r1}R_{r2}NH$ so as to give the amide compounds of formula ($III^1$) by N-acylation/amidation.

The first 2 steps are in particular described by Mata et al., *Carbohydr. Res.* 1990, 201, 223-31; Mata et al., *Carbohydr. Res.* 1992, 225, 159-61; Köll et al., *J. Carbohydr. Chem.* 2000, 19, 1019-47.

Alternatively, in certain cases, (in particular when $R_{r1}$ and $R_{r2}$ are alkyl groups), it may be possible to obtain amide compounds of formula ($III^1$) directly by means of a Lubineau reaction (step 1 b) between the monosaccharide or the polysaccharide of formula (IV) and an acetoacetamide compound of formula (VII). The reaction takes place in particular in the presence of a mineral base such as $M^+OH^-$, $M^+$ representing a cation, such as NaOH, or preferably of a weak base such as (bi)carbonate, in particular with an alkali metal (bi)carbonate, or in the presence of an organic base such as triethylamine or diisopropylethylamine, in particular in a polar protic solvent such as water, optionally by heating at a temperature between 30° C. and 100° C., in particular at between 50° C. and 60° C., preferably for a period of between 1 hour and 24 hours, in particular between 2 hours and 5 hours, such as 2 or 3 hours.

The compounds of formula (I) for which A denotes a hydrogen atom and the sugar is in furanose form may also be obtained according to scheme (2) below:

Scheme (2)

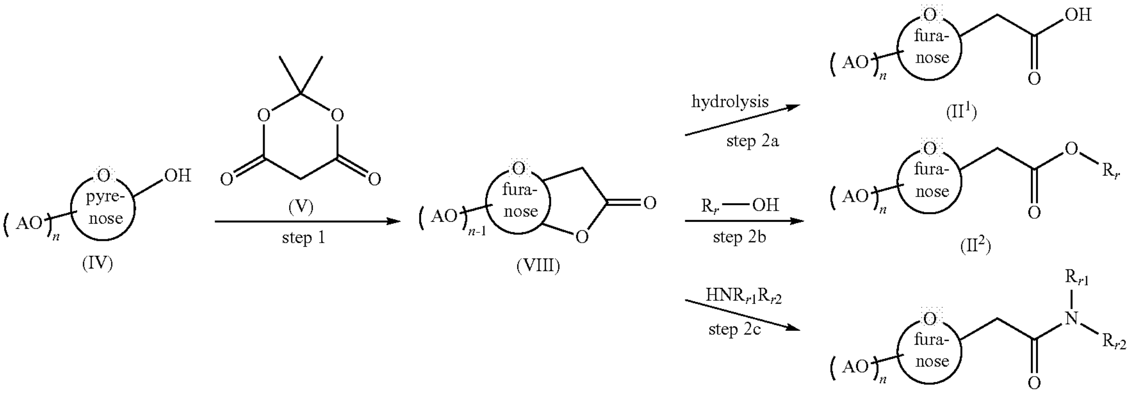

(IV) (VIII) ($II^1$) ($II^2$) ($III^1$)

between 30° C. and 120° C., in particular between 80° C. and 100° C., such as 100° C., for a period of between 2 h and 24 h, in particular between 2 h and 5 h, so as to give an acid C-glycoside compound ($II^1$).

Step 3 consists in reacting the acid ($II^1$) either with an alcohol $R_r$—OH so as to give the ester compounds of This alternative synthetic route comprises the following steps:

step 1 consists in reacting a monosaccharide or a polysaccharide of formula (IV) with Meldrum's acid (V), in particular in the presence of an organic base such as a tertiary amine, for instance triethylamine or tertbutylamine. Step 1 is performed in particular in a polar aprotic solvent such as DMF or acetonitrile, optionally heating to a temperature of between 30° C. and 100° C., in particular 45-49° C., preferably for a time of between 1 hour and 7 days, in particular between 2 and 7 days, such as 5 days, such as 5 days, to give a lactone intermediate fused with a sugar unit in furanose form (VIII);

step 2a consists in performing a hydrolysis of compound (VIII), especially in acidic medium, and in particular in dilute acidic medium as an aqueous solution such as hydrochloric acid, in a polar protic solvent such as water, optionally heating to a temperature of between 30° C. and 120° C., in particular between 80° C. and 100° C., such as 100° C., for a time of between 2 hours and 24 hours, to give a C-glycoside acid compound ($II^1$) in furanose form;

Alternatively, step 2 may also consist in opening the lactone (VIII) in aqueous basic medium, especially in the presence of a strong inorganic base such as sodium hydroxide or potassium hydroxide, in a polar protic solvent such as water, at room temperature or with heating optionally to a temperature of between 30° C. and 120° C., in particular between 80° C. and 100° C., such as 100° C., for a time of between 2 hours and 24 hours, to give a C-glycoside acid compound ($II^1$) in furanose form;

step 2b consists in performing opening of the lactone compound (VIII) with an alcohol $R_r$—OH, especially in acidic medium, such as in the presence of hydrochloric acid, in a polar aprotic solvent such as THF, dioxane or DMF (the alcohol $R_r$—OH may itself be used as solvent), optionally heating to a temperature of between 30° C. and 160° C., in particular between 80° C. and 120° C., such as 100° C., for a time of between 2 hours and 24 hours, to give a C-glycoside ester compound ($II^2$) in furanose form. Alternatively, the lactone (VIII) may be opened with the alcohol $R_r$—OH deprotonated beforehand with a strong base such as Na or NaH to form the corresponding alkoxide;

step 2c consists in performing opening of the lactone compound (VIII) with an amine $R_{r1}R_{r2}NH$, in a polar aprotic solvent such as THF, dioxane or DMF (the amine $R_{r1}R_{r2}NH$ may itself be used as solvent), optionally heating to a temperature of between 30° C. and 160° C., in particular between 80° C. and 120° C., such as 100° C., for a time of between 2 hours and 24 hours, to give a C-glycoside amide compound ($III^1$) in furanose form.

All the reagents are obtained by conventional methods known by those skilled in the art. The latter will take care to protect or deprotect according to the synthesis steps. It may be necessary to carry out a step of protecting the hydroxyl groups (groups A) and/or the amino groups (group $NR_bR_c$) of the sugar unit (IV), before the first step, and then to carry out the optional deprotection thereof after the third step. For example:

The compounds can be obtained from a sugar (IV) comprising OH group(s) which are free or substituted with a $C_1$-$C_6$ alkyl group or with a $C_1$-$C_6$ alkylcarbonyl group, or comprising an OH group protected by a protective group, said protective group being accessible according to the methods described by Peter G. M. Wuts and Theodora W. Greene, in Greene's Protective Groups in Organic Synthesis, Fourth Edition, Wiley, 2006; processes for alkylation or acylation of the hydroxyls of sugars are known and in particular described in Durantie, Estelle et al, Chemistry—A European Journal, 18(26), 8208-8215 (2012).

The sugar (IV) can also contain one or more amino group(s) substituted with the same $C_1$-$C_6$ alkylcarbonyl group, or with a PG such as those described by Peter G. M. Wuts and Theodora W. Greene, in *Greene's Protective Groups in Organic Synthesis*, Fourth Edition, Wiley, 2006. The processes for alkylation, or acylation of the hydroxyls of sugars are known by those skilled in the art and are in particular described in: Durantie, Estelle et al, *Chemistry—A European Journal,* 18(26), 8208-8215 (2012).

The step of alkylation of the hydroxyl group is generally carried out by treatment with a base, often a relatively strong base, of NaH, tBuOK or tBuONa type, in the presence of an alkylation agent such as an alkyl halide, in a non-protic polar solvent such as DMF, NMP, THF, ACN or acetone.

The N-acylation methods are also well known by those skilled in the art and consist in reacting the amine with either a reactive derivative of a carboxylic acid, such as an acid anhydride or an acid halide (acid chloride), or a carboxylic acid activated in situ via a coupling agent such as HOBt, EDCl, CDI, DCC, HATU or PyBOP, in the optional presence of an organic base such as DIEA or TEA, or of a mineral base such as NaOH, and optionally of DMAP in an equimolar or catalytic amount, in a non-protic polar solvent such as DCM, THF, DMF or ACN, or optionally a protic solvent such as water.

The esterification methods are generally carried out by treatment with alcohol, either a reactive derivative of a carboxylic acid, such as an acid anhydride or an acid halide (acid chloride), or a carboxylic acid activated in situ via a coupling agent such as HOBt, EDCl, CDI or DCC, optionally in the presence of a base such as pyridine, triethylamine or diisopropylethylamine, sodium acetate or sodium hydroxide, and optionally of DMAP in an equimolar or catalytic amount, in a non-protic polar solvent such as ACN, pyridine, DCM, THF or acetone, or optionally a protic solvent such as water. Alternatively, the hydroxyl can be treated with a carboxylic acid in an acid medium (APTS, anhydrous HCl, $H_2SO_4$), with a device for eliminating the water formed, such as the presence of a desiccant, for instance silica gel, $Na_2SO_4$, $MgSO_4$ or $P_2O_5$, or a Dean Stark apparatus using a volatile solvent which forms an azeotrope with water, for instance toluene or cyclohexane.

The present invention also relates to a composition comprising, in a physiologically acceptable medium, at least one compound of formula (I), and in particular at least one compound of formula (IIa), (IIb), (IIc), (IIIa), (IIIb), (IIIc), (IIId) and/or (IIIe) and more particularly at least one compound chosen from the compounds 2, 3, 4 and 5, as described above. The composition is in particular a cosmetic composition.

According to one advantageous form of the invention, the cosmetic composition contains at least one compound of formula (I), and in particular at least one compound of formula (IIa), (IIb), (IIc), (IIIa), (IIIb), (IIIc), (IIId) and/or (IIIe), and more particularly at least one compound chosen from the compounds 2, 3, 4 and 5, as previously defined, and at least one additive chosen from a fragrance, a thickener, a surfactant, a pigment, a dye and a preservative.

More particularly, the cosmetic composition according to the invention contains at least one compound chosen from the compounds 1 to 5, preferentially chosen from compounds 2, 3, 4 and 5 previously defined, and also the solvates thereof such as hydrates, and the organic or mineral acid or base salts thereof.

The compound of formula (I), and in particular the compounds of formula (IIa), (IIb), (IIc), (IIIa), (IIIb), (IIIc), (IIId) and/or (IIIe) defined above, (each compound of formula (I) if the composition comprises several thereof) can be present in the composition in an amount which can be between 0.01% and 20% by weight, preferably between 0.1% and 15% by weight, in particular between 0.5% and 10% by weight, relative to the total weight of the composition.

The composition also comprises a physiologically acceptable medium, which is preferably a cosmetically or pharmaceutically acceptable medium, in particular a dermatologically acceptable medium, i.e. a medium that has no unpleasant odour, colour or appearance, and that does not cause the user any unacceptable stinging, tautness or redness. In particular, the composition is suitable for topical application to the skin and skin integuments.

The term "physiologically acceptable medium" is intended to mean a medium that is compatible with human skin and skin integuments.

The composition according to the invention may then comprise water and/or any adjuvant commonly used in the envisaged application field.

Mention may be made in particular of: organic solvents, in particular $C_1$-$C_6$ alcohols and $C_2$-$C_{10}$ carboxylic acid esters; carbon-based and/or silicone oils, of mineral, animal and/or plant origin; water, waxes, pigments, fillers, colorants, surfactants, emulsifiers, coemulsifiers; cosmetic or dermatological active agents, UV-screening agents, polymers, hydrophilic or lipophilic gelling agents, thickeners, preservatives, fragrances, bactericides, odour absorbers and antioxidants.

These optional adjuvants may be present in the composition in a proportion of from 0.001% to 80% by weight and in particular from 0.1% to 40% by weight relative to the total weight of the composition.

The composition according to the invention may constitute a makeup composition, or preferably a skincare composition, and in particular a cleansing, protecting, treating or care cream for the face, the hands, the feet, the major anatomical folds or the body (for example day creams, night creams, makeup-removing creams, foundation creams or anti-sun creams); a fluid foundation, a makeup-removing milk, a protective or care body milk or an anti-sun milk; a skincare lotion, gel or mousse, such as a cleansing lotion, or a hair composition.

A subject of the invention is also a process for cosmetic treatment of keratin materials such as the skin, comprising the application, to these said materials such as the skin, of a composition comprising at least one compound of formula (I), and in particular the compounds of formulae (IIa), (IIb), (IIc), (IIIa), (IIIb), (IIIc), (IIId) and/or (IIIe) defined above, as previously defined.

In a particular embodiment, the treatment process aims to prevent the signs of skin ageing.

Preferably, the treatment process aims to treat the signs of skin ageing.

In a particular embodiment, it also relates to a process for cosmetic treatment of the skin intended to prevent and/or treat ageing, comprising at least one step which consists in applying to skin exhibiting signs of skin ageing at least one composition comprising a compound of formula (I) as defined previously.

In particular, the process according to the invention aims to improve the radiance and/or the uniformity of the complexion; to improve the radiance and/or the transparency of the skin; to improve the softness, the suppleness and/or the elasticity of the skin and/or the tonicity of the skin and/or the firmness of the skin; and/or to prevent and/or reduce wrinkles and/or fine lines.

In particular, the cosmetic treatment process aims to maintain and/or stimulate the moisturization and/or combat the drying out of the skin, and/or to maintain the barrier function of the skin.

In a particular embodiment, the compounds of formula (I), and in particular the compounds of formulae (IIa), (IIb), (IIc), (IIIa), (IIIb), (IIIc), (IIId) and/or (IIIe) defined above, are in particular useful as agents for combating the signs of ageing, in particular chronobiological ageing, of the skin.

The present invention also relates to the use of at least one compound of formula (I), and in particular the compounds of formulae (IIa), (IIb), (IIc), (IIIa), (IIIb), (IIIc), (IIId) and/or (IIIe) defined above, a salt thereof, or a solvate thereof, for preparing a composition intended for combating the signs of ageing, in particular chronobiological ageing, of keratin materials such as the skin. It also relates to the use of at least one compound of formula (I) as defined above, in a cosmetic composition comprising a physiologically acceptable medium, as an agent intended for combating the signs of ageing of keratin materials such as the skin, and/or as moisturizing agents for keratin materials such as the skin.

The present invention also relates to the use of a compound or of a composition according to the invention for combating the signs of ageing, in particular chronobiological ageing, of the skin, and/or for improving the moisturization of the skin.

The compounds or compositions according to the invention may be in particular intended for correcting all skin re-epithelialization disorders.

In a particular embodiment, the compounds or compositions according to the invention are particularly suitable for combating the signs of chronobiological ageing of the epidermis.

During chronobiological ageing, the thickness of the epidermis becomes reduced, the cell divisions decreasing in number. By facilitating cell multiplication, in particular epidermal cell multiplication, the regeneration of the epidermis is facilitated and the skin has a younger appearance.

In a particular embodiment, the compounds or compositions according to the invention are in particular intended for preventing or reducing wrinkles and fine lines, and/or thinning of the skin and/or the flaccid and/or withered skin appearance. The present invention thus also relates to the use of at least one compound according to the invention in a cosmetic composition for preventing or reducing wrinkles and fine lines, and/or thinning of the skin and/or the flaccid and/or withered skin appearance.

The invention is illustrated in greater detail by the following non-limiting examples.

EXAMPLES

Example 1: Synthesis of Compounds 2, 3, 4 and 5

Synthesis of Compound 2

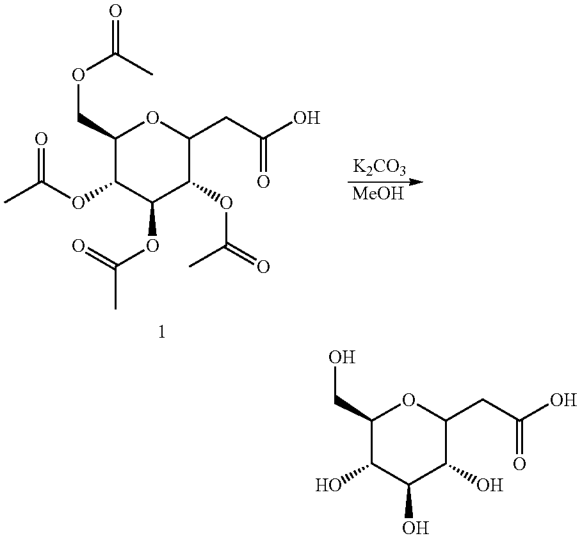

1

2

Compound 1 ([34010-29-2]/[267235-22-3]) is described for example by Mata et al., *Carbohydr. Res.* 1992, 225, 159-61.

$K_2CO_3$ (2.12 g, 15.37 mmol) is added to a solution of compound 1 (3 g, 7.69 mmol) in methanol (50 ml). The reaction mixture is stirred for 16 h at room temperature, and then adjusted to pH 4 with a 4 N aqueous HCl solution. After filtration, the filtrate is evaporated to dryness. The residue is purified by silica gel chromatography (dichloromethane/MeOH 10:1) to give the compound 2 (white solid, 1 g, yield=59%). The $^1H/^{13}C$ NMR spectra and the mass spectrometry are in accordance with the expected structure.

Synthesis of Compound 3

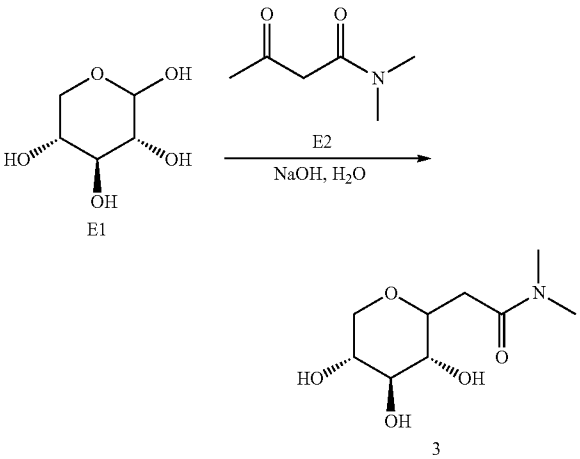

E1

E2

3

N,N-dimethylacetoacetamide E2 (1.40 ml, 8.0 mmol) is added dropwise to a solution of D-xylose E1 (1 g, 6.7 mmol) in water (2.0 ml). Sodium hydroxide (1.33 g in water at 30%) is then added dropwise while maintaining the temperature below 35° C. The reaction mixture is stirred for 45 min at 50° C., and then left to return to room temperature for 2 h 30. Butanol (1.52 g) and 37% HCl (1.41 g) are added (pH 1). After the addition of ethyl acetate (2.5 ml), the mixture is stirred for 30 min and then left to separate out. The operation is repeated with the addition of dichloromethane (2.5 ml). The residual aqueous phase is treated with 200 mg of vegetable black, and stirred for 15 min. The product is filtered through celite and rinsed with water. The filtrate obtained is neutralized to pH 10, and then concentrated under vacuum. The inorganic salts are precipitated by addition of ethanol and then filtration and concentration, and then again by addition of acetone. The filtrate obtained is then purified by silica gel chromatography (dichloromethane/MeOH 95:5 to 85:15). The residue obtained is precipitated from dichloromethane, filtered, washed with diisopropyl ether, then recrystallized from ethanol and dried under vacuum to give the compound 3 (white solid, 144 mg, yield=10%).

Synthesis of Compound 4

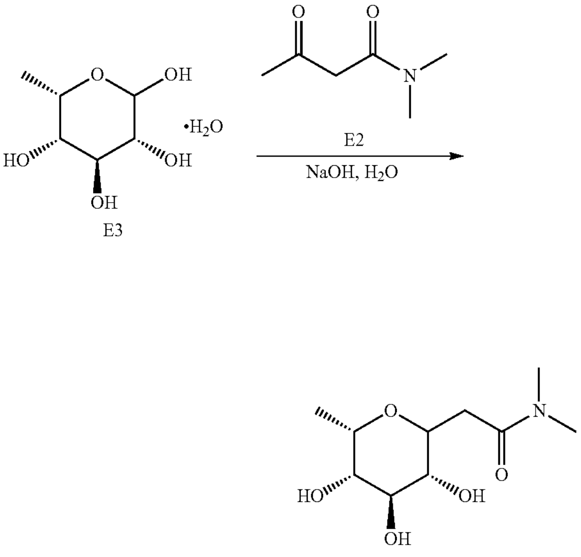

E3

E2

4

Sodium hydroxide (35% in water, 0.45 ml) is added to a solution of L-rhamnose E3 (1 g, 5.5 mmol) in N,N-dimethylacetoacetamide E2 (2.40 ml, 13.7 mmol). The reaction mixture is stirred for 1 h at 60° C., and then left to return to room temperature and diluted with water. The mixture is stirred for 30 min with a Dowex 500WX2-200 acid resin and then filtered. The aqueous phase is extracted 4 times with dichloromethane, and then concentrated under vacuum. The residue is purified by silica gel chromatography (EtOAc/MeOH 9:1). The product obtained is dissolved in water, washed once with dichloromethane (DCM), purified with animal black and then filtered through celite. The filtrate is rewashed twice with DCM and the aqueous phase is concentrated under vacuum. After the addition of ethanol, the precipitate formed is filtered off, then the filtrate is evaporated to dryness to give the compound 4 (dark green solid, 223 mg, yield=18%).

Synthesis of Compound 5

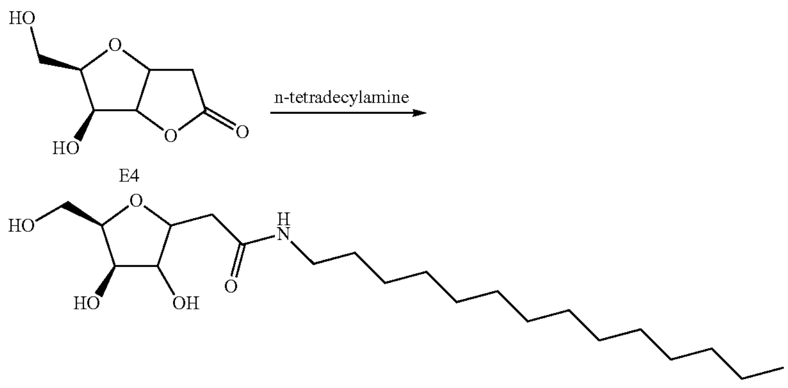

E4

5

Compound E4 is prepared according to P. Köll et al., J. Carbohydr. Chem. 2000, 19(8), 1019-47.

The lactone E4 (253 mg, 1.44 mmol) is added to n-tetradecylamine (1.54 g, 7.20 mmol) liquefied at 50° C. The reaction mixture is heated at 76° C. for 4 hours. After returning to room temperature, the mixture sets to a solid. It is taken up in ethyl acetate and the solid is then filtered off and washed with ethyl acetate. The operation is repeated twice. A white powder is obtained in a yield of 45%.

Example 2: Demonstration of the Depigmenting Effect of the Compounds of Formula (I) that are Suitable for Use in the Invention Protocol The efficacy was demonstrated on the basis of the following test:

The depigmenting activity (reduction of melanin production) of compounds of formula (I) was measured by assay in normal human melanocytes in vitro as follows.

First, normal human melanocytes are cultured and distributed in a multiple-well plate.

After 24 hours, the culture medium was replaced with a medium containing the compounds of formula (I) to be evaluated. The cells were incubated for 72 hours before measuring the final optical density, which measures the amount of melanin produced by the melanocytes. The measurement was calibrated and the compounds were tested at 100 μM.

Various test runs were performed and the results are collated in the following tables.

Results

The test results are summarized in table 1 below.

TABLE 1

| | % depigmentation at 100 μM | | |
|---|---|---|---|
| Compound | Run 1 | Run 2 | Run 3 |
| 1 | | | 24% |
| 2 | | 29% | |
| 4 | 15% | | |

From these results, it emerges that the compounds of formula (I) at low concentration have depigmenting properties.

Example 3: Composition According to the Invention

A skin depigmenting gel is prepared. It comprises the ingredients which follow (in weight % relative to the total weight of the composition):

| Ingredients | Weight % relative to the total weight of the composition |
|---|---|
| Compound 2 | 3 |
| Carbomer (sold under the name Carbopol ® 981 by the company Lubrizol) | 1 |
| Preserving agent | qs |
| Water | qs 100 |

The composition according to the invention applied to the skin makes it possible to homogenize the complexion, in particular to fade out brown spots.

Example 4

An anti-ageing gel for the skin is prepared, comprising (% by weight):

| | |
|---|---|
| compound 2 | 2% |
| hydroxypropylcellulose (Klucel H from Hercules) | 1% |
| fragrance, preservative | qs |
| isopropanol | 40% |
| water | qs 100% |

A similar composition is prepared with the compound 3.

This composition can be applied to the face each day, in particular for several weeks.

The invention claimed is:

1. A process for depigmenting, lightening and/or bleaching keratin material, and/or for improving homogeneity and/or reviving radiance of the complexion of the skin or of the complexion of semi-mucous membranes, which comprises applying to the keratin material of a subject in need thereof and/or desirous of depigmenting, lightening and/or bleaching keratin material, and/or for improving homogeneity and/or reviving radiance of the complexion of the skin or of the complexion of semi-mucous membranes, an effective amount of at least one compound chosen from the group of Compound 1:

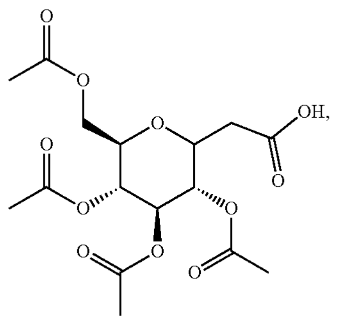 [SMILES: CC(=O)OC[C@H]1OC(CC(=O)O)[C@H](OC(C)=O)[C@@H](OC(C)=O)[C@@H]1OC(C)=O]

the salts, isomers, and solvates thereof and mixtures thereof.

2. The process according to claim 1, wherein the keratin material is skin.

3. The cosmetic treatment process as claimed in claim 1 which comprises preventing, reducing and/or treating an impairment in the complexion of the skin or the complexion of semi-mucous membranes, wherein the keratin material is facial and/or bodily skin.

4. The process as claimed in claim 1, wherein the keratin material is skin and which comprises bleaching, lightening and/or depigmenting skin.

5. The process as claimed in claim 1, being for depigmenting, lightening and/or bleaching keratin material wherein the subject is in need of depigmenting, lightening and/or bleaching keratin material or desirous of depigmenting, lightening and/or bleaching keratin material.

6. The process as claimed in claim 1, being for depigmenting and/or for treating skin aging wherein the subject is in need of depigmenting and/or treatment of skin aging or desirous of depigmenting, lightening and/or treatment of skin aging.

* * * * *